United States Patent
Asafusa et al.

(10) Patent No.: US 7,698,948 B2
(45) Date of Patent: Apr. 20, 2010

(54) ULTRASONIC DIAGNOSTIC APPARATUS

(75) Inventors: Katsunori Asafusa, Kashiwa (JP); Ryuichi Shinomura, Higashimatsuyama (JP)

(73) Assignee: Hitachi Medical Corporation, Tokyo (JP)

( * ) Notice: Subject to any disclaimer, the term of this patent is extended or adjusted under 35 U.S.C. 154(b) by 758 days.

(21) Appl. No.: 10/581,486

(22) PCT Filed: Dec. 1, 2004

(86) PCT No.: PCT/JP2004/017866

§ 371 (c)(1),
(2), (4) Date: Jun. 26, 2006

(87) PCT Pub. No.: WO2005/058167

PCT Pub. Date: Jun. 30, 2005

(65) Prior Publication Data

US 2008/0229833 A1  Sep. 25, 2008

(30) Foreign Application Priority Data

Dec. 2, 2003 (JP) .............................. 2003-402936
Jun. 14, 2004 (JP) .............................. 2004-175639

(51) Int. Cl.
G01N 29/44 (2006.01)
A61B 8/00 (2006.01)

(52) U.S. Cl. .............................. 73/627; 73/606; 73/628; 600/443; 600/447

(58) Field of Classification Search .................. 73/627, 73/628, 606; 600/437, 440, 441, 447
See application file for complete search history.

(56) References Cited

U.S. PATENT DOCUMENTS

| | | | | | |
|---|---|---|---|---|---|
| 4,543,547 | A | * | 9/1985 | Picquendar et al. | 333/193 |
| 4,569,231 | A | * | 2/1986 | Carnes et al. | 73/626 |
| 5,454,371 | A | * | 10/1995 | Fenster et al. | 600/443 |
| 6,213,947 | B1 | * | 4/2001 | Phillips | 600/443 |
| 7,020,183 | B2 | * | 3/2006 | Nakamura | 375/150 |
| 7,354,400 | B2 | * | 4/2008 | Asafusa et al. | 600/437 |
| 7,445,642 | B2 | * | 11/2008 | Amos et al. | 623/23.68 |
| 2008/0154133 | A1 | * | 6/2008 | Shiki | 600/443 |

FOREIGN PATENT DOCUMENTS

| | | |
|---|---|---|
| JP | 04-009658 | 1/1992 |
| JP | 2002-233526 | 8/2002 |
| JP | 2002-345813 | 12/2002 |
| JP | 2003-153904 | 5/2003 |

* cited by examiner

Primary Examiner—J M Saint Surin
(74) Attorney, Agent, or Firm—Antonelli, Terry, Stout & Kraus, LLP.

(57) ABSTRACT

Encoded transmission and reception which reduces time side lobe are realized while suppressing increase of circuit scale. Transmission signals corresponding to a composite modulation code sequence composed from two or more modulation code sequences are outputted as transmission signals. A reception means demodulates reception signals stepwise by two or more demodulators. The demodulator can be thereby divided into two or more stages, and therefore with a circuit scale corresponding to the sum of the operation circuit numbers of two or more demodulators, time side lobe reduction effect can be obtained at a level equivalent to that obtainable with a circuit scale corresponding to the product of the operation circuit numbers of two or more demodulators.

18 Claims, 19 Drawing Sheets

FIG. 3
BARKER CODE
code1=(+1,+1,+1,−1,+1) L1=5
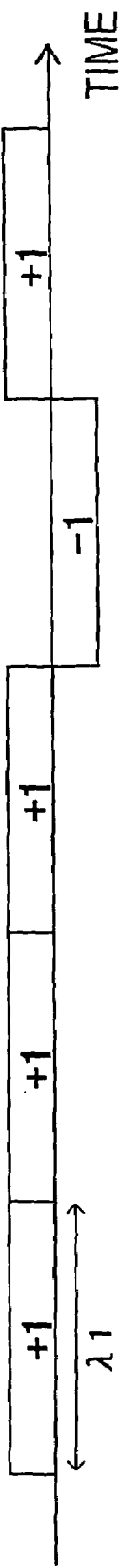
BARKER CODE (GOLAY CODE)
code2=(+1,+1,−1,+1) L2=4
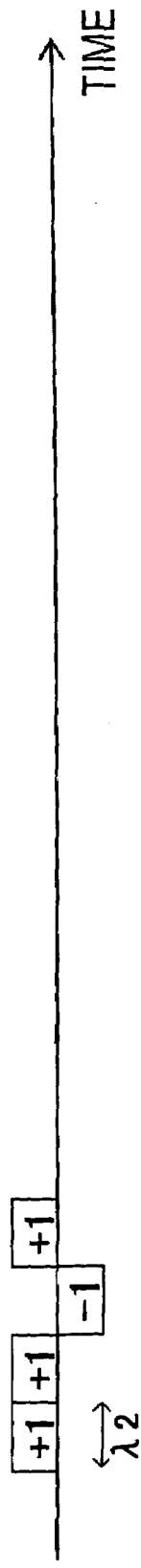
codeX=[(+1,+1,−1,+1), (+1,+1,−1,+1), (+1,+1,−1,+1), (−1,−1,+1,−1), (+1,+1,−1,+1)] Lx=20
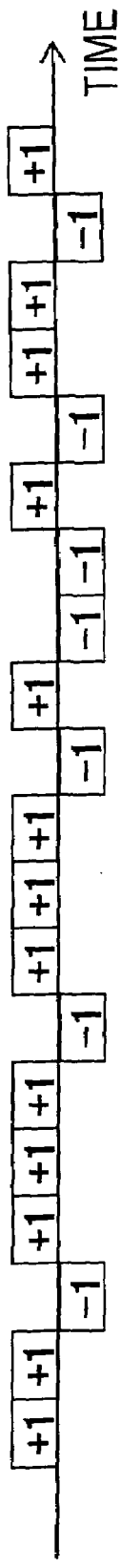

FIG. 9
(a)
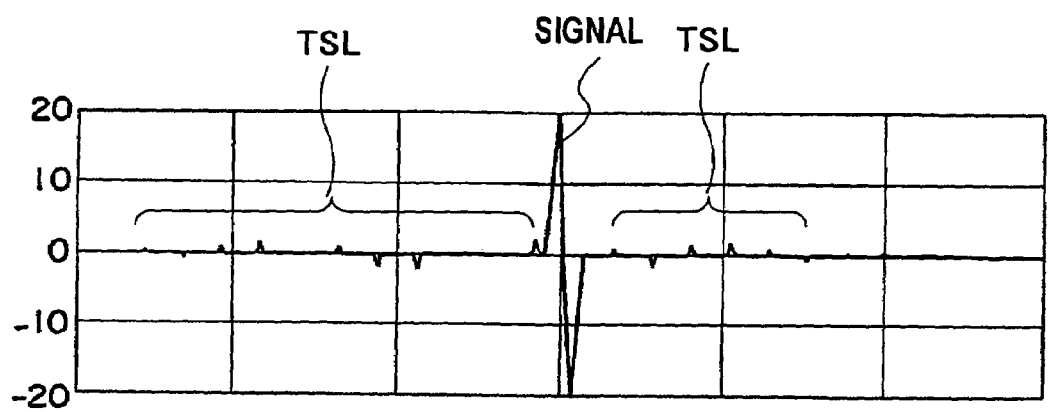
(b)
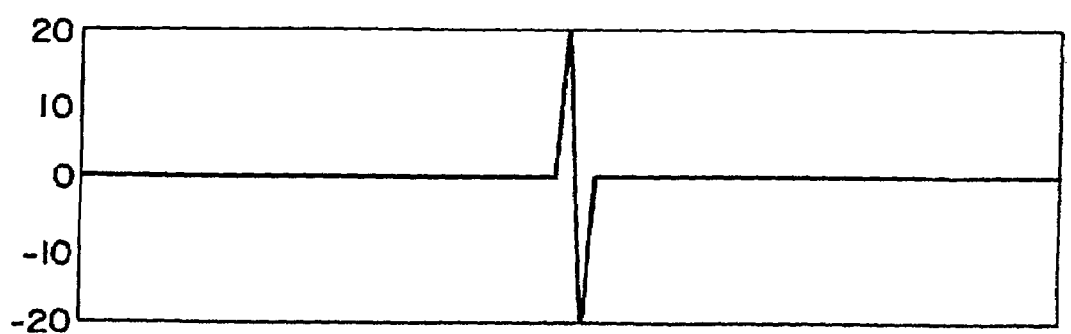

FIG. 14
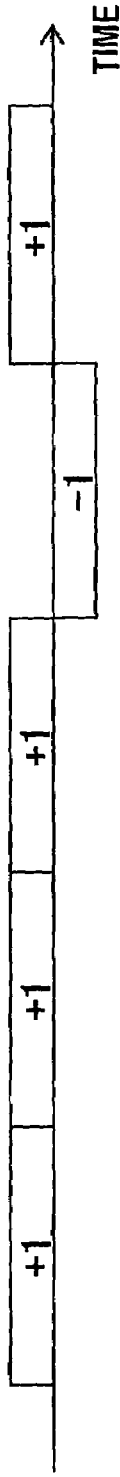
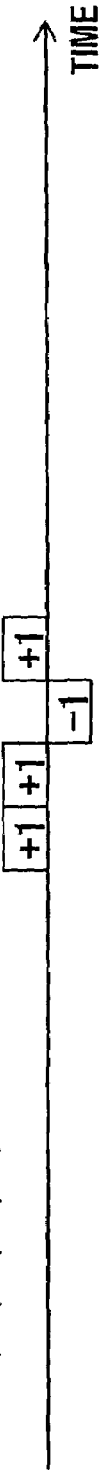
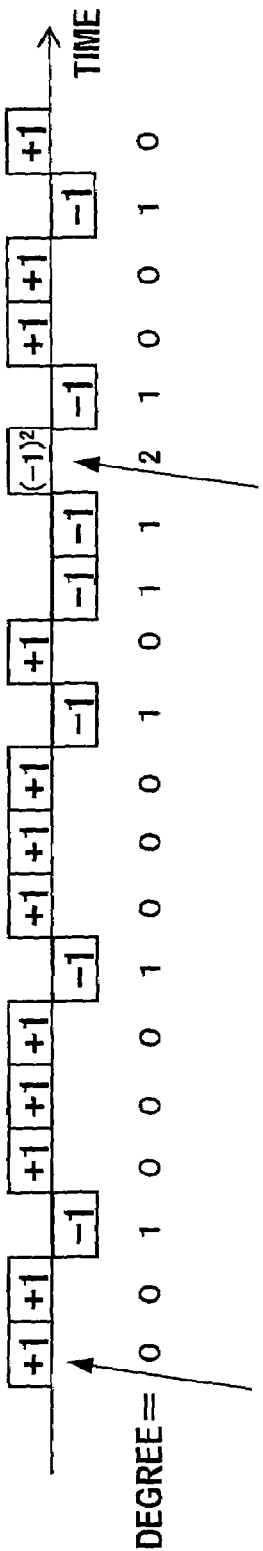

FIG. 16
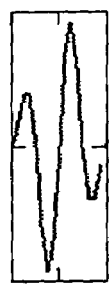   
FUNDAMENTAL    0°                90°                180°              270°
WAVE

ULTRASONIC DIAGNOSTIC APPARATUS

FIELD OF THE INVENTION

The present invention relates to an ultrasonic diagnostic apparatus which performs encoded transmission and reception.

BACKGROUND OF THE INVENTION

An ultrasonic diagnostic apparatus outputs driving signals from a transmission means so as to transmit ultrasonic waves from a probe on an object to be inspected, receives echo signals reflected by the object with the probe, and reconstructs an ultrasonogram (ultrasonic image) on the basis of the received signals. The probe consists of an array of oscillators, and the focal position of the ultrasonic waves in the object can be controlled by adding predetermined time lags to received signals of the oscillators upon receiving of ultrasonic waves. The method of shifting a focal position by changing the time lags is called dynamic focus.

It is desirable on an ultrasonic diagnostic apparatus that the waveform of the transmitted ultrasonic wave should be a pulse wave which is short in the direction of the time axis in order to improve the depth resolution, and have a large signal intensity in order to improve the SN ratio (Signal Noise Ratio). However, it is necessary to control the maximum intensity of the ultrasonic waves to such a level that they should not affect living bodies. Therefore, in order to increase transmission energy with suppressing the maximum intensity of ultrasonic waves, it is described in, for example, Japanese Patent Unexamined Publication (KOKAI) No. 2003-225237 and so forth to apply an encoded transmission technique widely used in the field of radars also to ultrasonic diagnostic apparatuses. In this technique, a single pulse waveform having a large peak intensity is diverged into a sequence along the time axis direction of signals each having a small peak intensity and transmitted to an object, signals reflected in the object are received, and then a decoding operation is performed with a demodulation filter to converge the signals along the time axis direction and thereby restore them into the pulse waveform having a large peak intensity.

As the code, the Barker code, Golay code and the like widely known in the field of radars can be used, and as the decoding filter, an autocorrelation filter, which performs autocorrelation operation, a mismatched filter, and so forth can be used.

Patent document 1: Japanese Patent Unexamined Publication (KOKAI) No. 2003-225237

DESCRIPTION OF THE INVENTION

Problems to be Solved by the Invention

However, with the conventional encoded transmission/reception techniques, when the ultrasonic energy diverged along the time axis direction by coding is converged by decoding, ultrasonic energies remain before and behind the pulse waveform originally intended to be obtained along the time axis direction to make a problem of generation of undesired signals called time side lobe. Although it is possible to reduce the time side lobe by using a high order filter using a large number of operations (degree) as the demodulation filter, the circuit scale increases for the large number of operations.

Moreover, if the number of code elements is increased in order to efficiently diverge the ultrasonic energy, reception signals will become longer along the time axis direction corresponding to the number of code elements. For this reason, it becomes more likely that intermittent switching operations such as switching of focal stage of dynamic focus is performed in the middle of a reception signal, and there is caused a phenomenon that the time side lobe is generated in a reception signal at a high level due to a switching operation.

The object of the present invention is to realize encoded transmission and reception which can be performed with reduced time side lobe and suppressing increase of circuit scale.

Means for Achieving the Object

In order to achieve the aforementioned object, the ultrasonic diagnostic apparatus of the present invention comprises a probe which transmits and receives ultrasonic waves to and from an object to be inspected, a transmission means which outputs transmission signals for driving the probe, a reception means which processes reception signals received by the probe, and an image reconstruction means which reconstructs an ultrasonogram using the reception signals outputted by the reception means. The transmission means creates and outputs the transmission signals corresponding to a composite modulation code sequence composed from two or more modulation code sequences. The reception means is provided with a demodulator which demodulates the modulation based on the composite modulation code sequence for the reception signals. By using a composite modulation code sequence composed from two or more modulation code sequences as described above, it becomes possible to demodulate the composite modulation code sequence stepwise with demodulators provided in two or more stages. Therefore, with a circuit scale corresponding to the sum of the numbers of operation circuits of the demodulators of two or more stages, the side lobe reduction effect can be obtained with a level equivalent to that obtainable with a circuit scale corresponding the product of the numbers of operation circuits of two or more stages.

The aforementioned transmission means may generate transmission signals by successively outputting waveforms on the basis of coefficients of code elements of the composite modulation code sequence.

As the aforementioned composite modulation code sequence, a composite modulation code sequence composed from a first modulation code sequence and a second modulation code sequence may be used. In such a case, the reception means has a first demodulator for demodulating the modulation based on the first modulation code sequence for the reception signals, and a second demodulator for demodulating the modulation based on the second modulation code sequence for the reception signals. The reception signals are demodulated by one of the first and second demodulators, and then further demodulated by the other demodulator.

In this embodiment, as the code interval of the first modulation code sequence, a code interval larger than that of the second modulation code sequence can be used. In this case, the first demodulator can be disposed on the probe side of the second demodulator, and the reception signals outputted from the probe can be demodulated by the first demodulator and then further demodulated by the second demodulator. With this configuration, a modulation code with a larger code interval is demodulated previously. Therefore, demodulation errors due to influence of discontinuous operations performed thereafter such as change of the focal stage, change of the number of apertures and change of the amplification factor can be reduced, and the time side lobe caused by such discontinuous operations can be reduced.

For example, the first demodulator can be disposed at a position for demodulating the reception signals before phasing addition thereof performed in the phasing addition means, which switches the focal stage, and the second demodulator can be disposed at a position for demodulating the reception signals after phasing addition in the phasing addition means. This makes it possible to reduce the demodulation error due to the change of the focal stage, and reduce the time side lobe. In addition, because the second demodulator is disposed after the phasing addition means, the circuit scale can also be markedly reduced.

Moreover, it is also possible to dispose both the first and second demodulators at a position for demodulating the reception signals after phasing addition in the phasing addition means. Because only one each of the first and second demodulators suffice for this configuration, the circuit scale is markedly reduced.

Further, it is also possible to dispose each of the first and second demodulators at a position for demodulating the reception signals before phasing addition in the phasing addition means. In this case, demodulation error due to change of focal stage is not caused, and therefore the time side lobe can be reduced. For this configuration, demodulators of the same number as that of the oscillators are required. However, because the demodulators are disposed as two stages, the circuit scale can be reduced compared with one-stage configuration.

The code length of the first modulation code sequence may be equivalent to or shorter than the code interval of the code elements constituting the second modulation code sequence. In this case, the coefficients of the code elements constituting the composite modulation code sequence can be obtained by multiplying the coefficient of each code element of the second modulation code sequence with the coefficients of all the code elements constituting the first modulation code sequence.

As for the configuration of the aforementioned transmission means, it can comprise a code storage means in which coefficients of multiple kinds of modulation code sequences are stored beforehand, selection means which selects the first modulation code sequence and the second modulation code sequence from those stored in the code storage means, and a composing means which composes the first and second modulation code sequences with adjusting the coefficients of the first and second modulation code sequences to desired code intervals to generate a composite modulation code sequence. In this case, the first and second modulation code sequences can be freely chosen depending on a state of an imaging site or as desired by a user.

Further, as another configuration of the aforementioned transmission means, it may comprise a composite code storage means in which multiple kinds of the aforementioned composite modulation code sequences are stored beforehand, and a selection means which selects one composite modulation code sequence from those stored in the composite code storage means. This configuration has an advantage of simple circuit configuration.

Further, the ultrasonic diagnostic apparatus according to another embodiment of the present invention comprises a probe which transmits and receives ultrasonic waves to and from an object to be inspected, a transmission means which outputs transmission signals for driving the probe, a reception means which processes reception signals received by the probe to obtain reception signals of which harmonics are emphasized, and an image reconstruction means which reconstructs an ultrasonic harmonic image using the reception signals outputted by the reception means. The transmission means creates and outputs the transmission signals corresponding to a composite modulation code sequence composed from two or more modulation code sequences and having phase shift amounts with respect to the fundamental wave as values of code elements. The reception means is provided with a demodulator which demodulates the modulation based on the composite modulation code sequence for the reception signals. By using such a composite modulation code sequence having phase shift amounts with respect to the fundamental wave as values of code elements as described above, it becomes possible to obtain reception signals of which harmonics are emphasized. In addition, because the demodulator is divided into multiple stages, the side lobe reduction effect can be obtained with reducing the circuit scale.

The aforementioned transmission means may generate the transmission signals by successively outputting waveforms representing phase shift amounts as values of elements of the composite modulation code sequence.

As the composite modulation code sequence, a composite modulation code sequence composed from a first modulation code sequence and a second modulation code sequence may be used. In such a case, the reception means has a first demodulator for demodulating the modulation based on the first modulation code sequence for the reception signals, and a second demodulator for demodulating the modulation based on the second modulation code sequence for the reception signals. The reception signals are demodulated by one of the first and second demodulators, and then further demodulated by the other demodulator.

When the coefficients of the code elements of the first and second modulation code sequences are two values of +1 and −1, the phase shift amounts as the values of the code elements of the composite modulation code sequence may be phase shift amounts corresponding to degrees of multiplied −1 in multiplication of the first and second modulation code elements.

In the above operation, the code elements of the composite modulation code sequence may be the phase shift amounts determined as $(180°/M) \times N$, wherein M is a degree of harmonic to be emphasized, and N is the aforementioned degree of −1.

The reception means may comprise a filter for eliminating fundamental wave components from the reception signal demodulated by the first and second demodulators. The fundamental wave components can be thereby eliminated to further emphasize the harmonic components.

The transmission means may output waveform signals of the composite modulation code sequence and waveform signals of another composite modulation code sequence in which the phase shift amounts of the code elements of the composite modulation code sequence are each further shifted by a predetermined amount of phase. The reception means may have a reception signal composing means which offsets fundamental wave components by composing reception signals of waveform signals first outputted among the transmission signals of two of the composite modulation code sequences with reception signals of waveform signals outputted afterward. The fundamental wave components can be thereby offset, and harmonic components can be further emphasized.

For example, the transmission means may comprise a storage means which stores the first and second modulation code sequences, a phase difference determination means which receives the first and second modulation code sequences from the storage means to count the degree of −1 and assigns a predetermined phase shift amount depending on the degree, and a waveform storage means which stores multiple kinds of waveforms corresponding to predetermined phase shift amounts and outputs a waveform corresponding to the phase shift amount determined by the phase difference determination means as transmission signals. Further, as another configuration of the transmission means, it may comprise a composite code storage means which stores multiple kinds of composite modulation code sequences beforehand, and a selection means which selects one composite modulation code sequence from those stored in the composite code storage means.

As the code interval of the first modulation code sequence, a code interval larger than that of the second modulation code sequence can be used. In this case, the first and second demodulators can be disposed so that the reception signals outputted from the probe should be demodulated by the first demodulator and then demodulated by the second demodulator. With this configuration, a modulation code with a larger code interval is demodulated first. Therefore, demodulation errors due to influence of discontinuous operations performed thereafter such as change of the focal stage, change of the number of apertures and change of the amplification factor can be reduced, and the time side lobe caused by discontinuous operations can be reduced.

For example, the first demodulator can be disposed at a position for demodulating the reception signals before phasing addition thereof in the phasing addition means, and the second demodulator can be disposed at a position for demodulating the reception signals after the phasing addition. This makes it possible to reduce demodulation errors due to the change of the focal stage, and reduce the time side lobe. In addition, because the second demodulator is disposed behind the phasing addition means, the circuit scale can also be markedly reduced.

Moreover, it is also possible to dispose both the first and second demodulators at a position for demodulating the reception signals after phasing addition thereof in the phasing addition means. Because only one each of the first and second demodulators suffice also for this case, the circuit scale is markedly reduced.

Further, it is also possible to dispose each of the first and second demodulators at a position for demodulating the reception signals before phasing addition by the phasing addition means. In this case, demodulation errors due to change of focal stage is not caused, and therefore the time side lobe can be reduced. Further, because the demodulators are disposed as two stages, the circuit scale can be reduced compared with one-stage configuration.

Advantages of the Invention

According to the present invention, encoded transmission and reception can be realized with reduced time side lobe and suppressing increase of circuit scale.

BRIEF DESCRIPTION OF THE DRAWINGS

FIG. 1 is a block diagram of the ultrasonic diagnostic apparatus according to the first embodiment of the present invention.

FIG. 2 is a block diagram of the transmission means 12 shown in FIG. 1.

[FIG. 3]

FIG. 3 is an explanatory diagram for explaining the composite modulation code, codeX, composed by the code composing means 56 shown in FIG. 2.

FIG. 4 is a block diagram of the first demodulator 40 and the second demodulator 44 shown in FIG. 1.

FIG. 5 is a diagram showing waveforms of reception signals and waveforms of decoding code, decode1, which are demodulated by the first demodulator 40 shown in FIG. 4.

FIG. 6 is a diagram showing waveforms of reception signals and waveforms of decoding code, decode2, which are demodulated by the second demodulator 44 shown in FIG. 5.

FIG. 7(a) is a graph showing a signal waveform obtained by demodulating reception signals with one step of a demodulation filter of 63 taps as a comparative example, FIG. 7(b) is a graph showing a signal waveform obtained by demodulating reception signals with one step of a demodulation filter of 131 taps as a comparative example, and FIG. 7(c) shows a graph showing a signal waveform obtained by demodulating reception signals with two steps of the demodulators 40 and 44 each of 31 taps by the configuration of the first embodiment.

FIG. 8(a) is an explanatory diagram for explaining discontinuous operation caused due to different focal data used before and after switching of the focal stage, and FIG. 8(b) is an explanatory diagram for explaining demodulation error caused by focal stage changing operation occurring in the middle of the code element D of code1 as the code codeX shown in FIG. 3(a).

[FIG. 9]

FIG. 9(a) is a graph showing time side lobe generated in the reception signals due to the demodulation error of the code element D shown in FIG. 8(a), and FIG. 9(b) is a graph showing a signal waveform in case that such a demodulation error does not occur.

FIG. 10 is a block diagram showing disposition of the first and second demodulators 40 and 44 according to the second embodiment of the present invention.

FIG. 11 is a block diagram showing disposition of the first and second demodulators 40 and 44 according to the third embodiment of the present invention.

FIG. 12 is a block diagram showing the configuration of the transmission waveform generation means 24 according to the forth embodiment of the present invention.

FIG. 13(a) is a block diagram showing the configuration of the transmission means 12 according to the fifth embodiment of the present invention, and FIG. 13(b) is a block diagram showing the configuration of the signal processing means 46 according to the fifth embodiment of the present invention.

[FIG. 14]

FIG. 14 is an explanatory diagram showing that the phase modulation means 130 shown in FIG. 13 counts the degree of −1 for the code elements of codeX.

FIG. 15 is an explanatory diagram showing codeY generated from the degree of codeX by the phase modulation means 130 shown in FIG. 13 and the transmission waveform of codeY.

[FIG. 16]

FIG. 16 is an explanatory diagram showing waveforms of the fundamental wave as well as those with phases of 90°, 180° and 270° stored beforehand in the waveform storage means 26 shown in FIG. 13.

FIG. 17 is a block diagram showing the configuration of the transmission means 12 according to the sixth embodiment of the present invention.

FIG. 18 is a block diagram showing the configuration of the signal processing means according to the sixth embodiment of the present invention.

FIG. 19 is an explanatory diagram showing codeY which is generated by the phase modulation means 130 shown in FIG. 17, codeZ which is generated by the second code generation means, and transmission waveforms thereof.

BEST MODE FOR CARRYING OUT THE INVENTION

First Embodiment

The ultrasonic diagnostic apparatus according to the first embodiment of the present invention will be explained with reference to FIGS. 1 to 9. In this embodiment, two kinds of modulation codes are composed to form a composite modulation code, and encoded transmission and reception are performed by using the composite modulation code.

Figure 1:
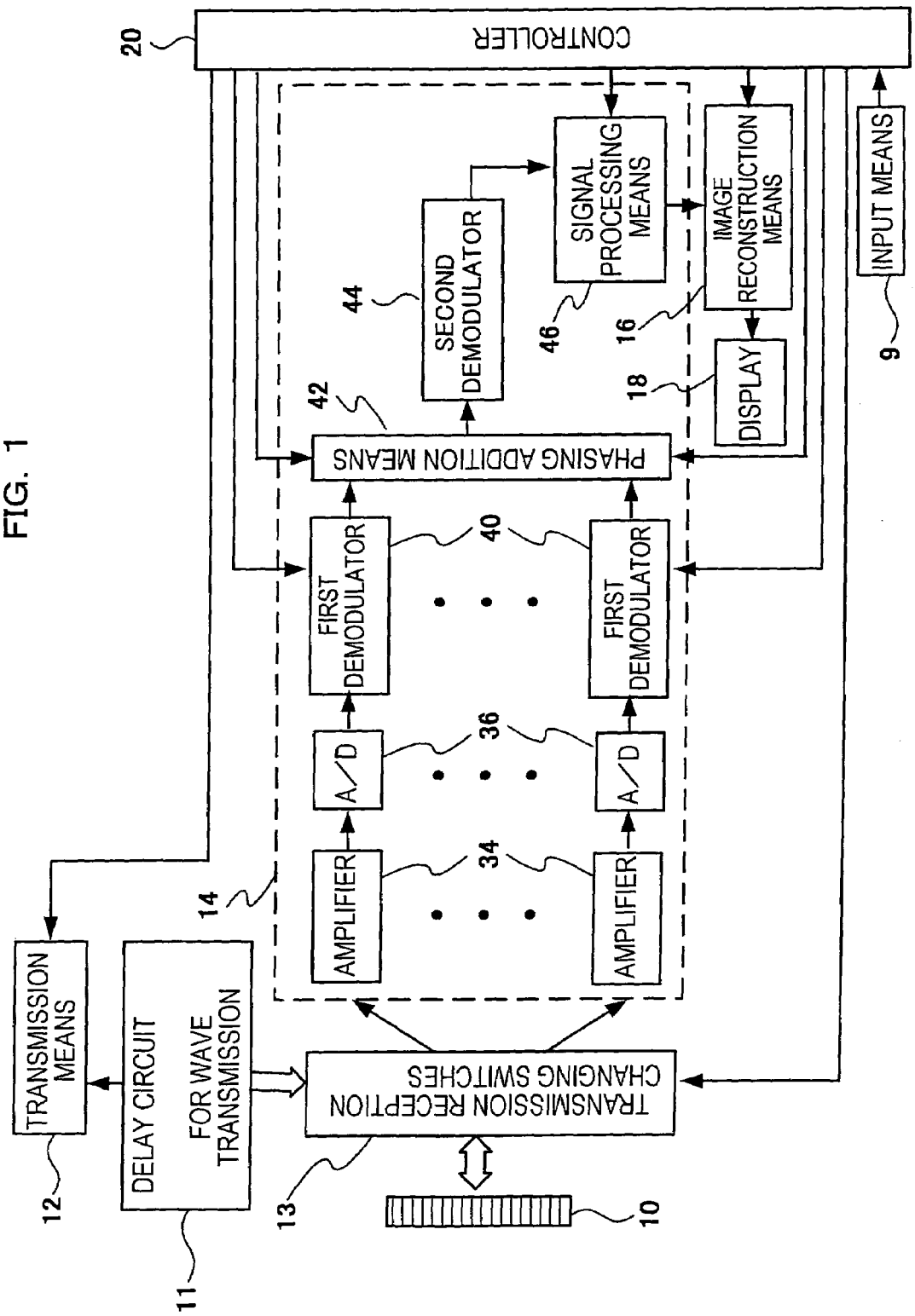
[FIG. 1]

FIG. 1 is a block diagram showing the whole configuration of an ultrasonic diagnostic apparatus of this embodiment. As shown in FIG. 1, the ultrasonic diagnostic apparatus is provided with a probe 10 which transmits and receives ultrasonic waves to and from an object to be inspected, a transmission means 12, a delay circuit 11 for wave transmission, transmission/reception changing switches 13, a reception means 14, an image reconstruction means 16, a display 18, a controller 20, and an input means 9. The transmission means 11 generates encoded transmission signals under control of the controller 20. The delay circuit 11 for wave transmission delays each of the transmission signals generated by the transmission means for a predetermined time according to directions of the controller 20. Transmission/reception changing switches 13 deliver transmission signals to each oscillator in variable apertures determined by the controller 20. Ultrasonic waves are thus transmitted toward a predetermined position of an object from each oscillator, and scanning and focusing upon transmission are performed. The ultrasonic waves reflected or scattered in the object are received by each oscillator of the probe 10 and converted into reception signals, and the reception signals are delivered to the reception means 14 by the transmission/reception changing switches 13 and decoded, and they are subjected to phasing and addition operations for the focusing operation at the time of wave reception. The image reconstruction means 16 reconstructs an ultrasonogram (for example, B-mode image, M-mode image etc.) on the basis of output signals of the reception means 14. The reconstructed ultrasonogram is displayed on the display 18. The controller 20 receives imaging conditions set by an operator from the input means 9 and controls the transmission means 12, the delay circuit 11 for wave transmission, the wave transmission/reception changing switches 13, the reception means 14, and the image reconstruction means 16, respectively.

Figure 2:
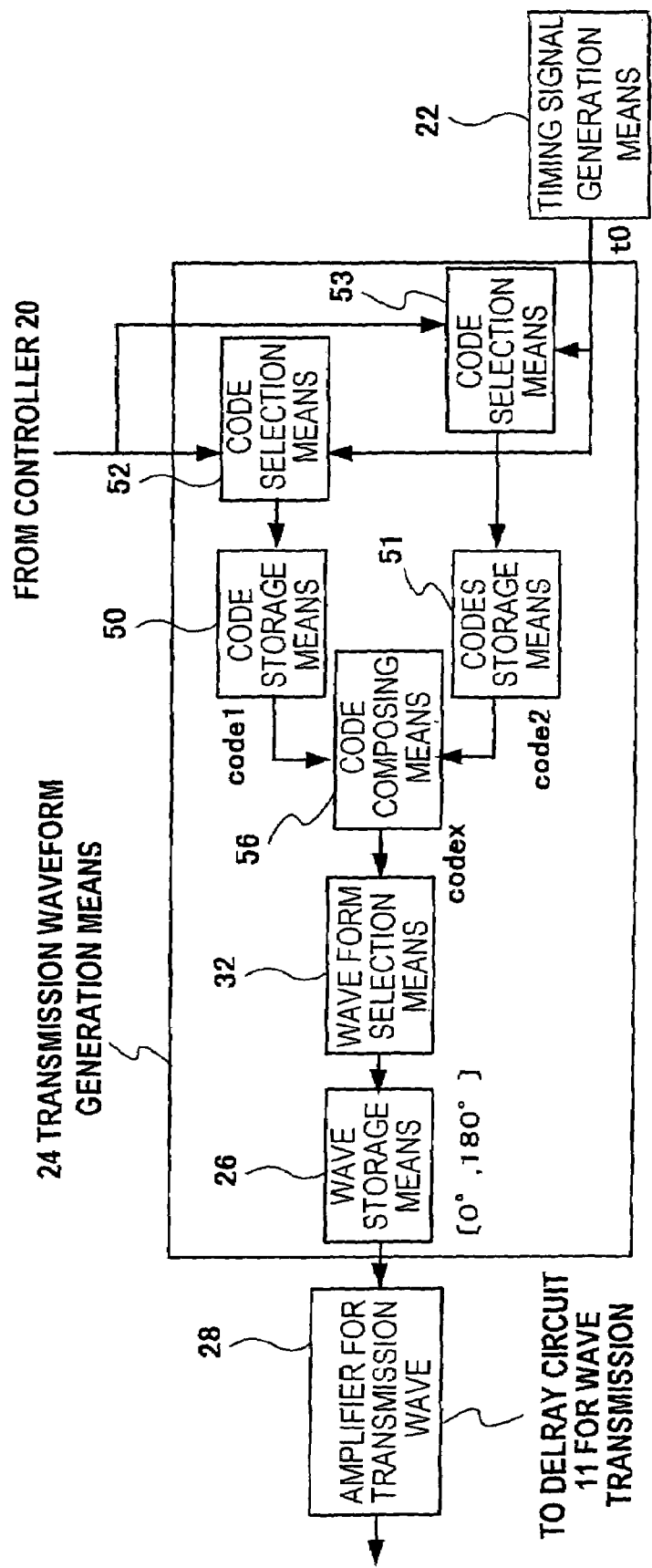
[FIG. 2]

The configuration of the transmission means 12 will be explained with reference to FIG. 2. The transmission means 12 comprises a timing signal generation means 22, a transmission waveform generation means 24 which generates a composite modulation code composed from at least two modulation codes and generates a waveform corresponding to the composite modulation code, and a wave transmission amplifier 28 which amplifies the transmission waveform outputted by the transmission waveform generation means 24 to generate transmission signals.

In this embodiment, the transmission waveform generation means 24 generates a composite modulation code composed from two modulation codes. For this purpose, it comprises code selection means 52 and 53, code storage means 50 and 51, a code composing means 56, a waveform output direction means 32, and a waveform storage means 26. Multiple kinds of modulation codes are stored beforehand in the code storage means 50 and 51, respectively. As the stored modulation codes, for example, Barker codes, Golay codes and Chirp codes of various code lengths (numbers of code elements) as well as various kinds of other known codes used for encoded transmission and reception can be used, and two or more kinds of desired codes among those are stored beforehand in the code storage means 50 and 51. The codes stored in the code storage means 50 and the codes stored in the code storage means 51 may be those of the same kind or different kinds.

The code selection means 52 and 53 receive directions for selecting the kinds of two modulation codes which are desired by a user to be used for the measurement, i.e., a first modulation code (code1) and a second modulation code (code2) from the controller 20. In this example, Barker codes with a code element number L1=5 (code sequence of +1, +1, +1, −1, +1) are selected as code1, and Barker codes with a code element number (code length) L2=4 (code sequence of +1, +1, −1, +1) are selected as code2, as shown in FIG. 3, for example. The code selection means 52 specifies an address number of the code1 among the two or more modulation codes stored in the code storage means 50, and directs the code storage means 50 to output signals representing the coefficients (+1 or −1) of the code elements of code1 with a predetermined time interval (called "code interval") of $\lambda 1$. The code selection means 53 specifies an address number of code2 among the two or more modulation codes stored in the code storage means 51, and directs the code storage means 51 to repeatedly output signals representing the coefficients of the code elements with a code interval of $\lambda 2$ for the number of times corresponding to the code element number L1 (L1=5). In this operation, $\lambda 1$ is set as a time equal to or longer than the code interval $\lambda 2$ of code2 multiplied with the code element number L2 of code2, $\lambda 2 \times L2$.

The code composing means 56 multiplies the signals successively received from the code storage means 50 and representing the coefficients (+1 or −1) of the code elements with the signals successively received from the code storage means 51 and representing the coefficients (+1 or −1) of the code elements to generate a composite modulation codeX composed from two modulation codes. That is, the composite modulation codeX corresponds to a code obtained by modulating each of the coefficients of the code elements of the code1 with all the code elements of code2, as shown in FIG. 3. The code element number Lx of the composite modulation code, codeX, is represented as $Lx = L1 \times L2 = 20$.

<Modulation Codes of Composite Modulation Code, Codex>

Modulation code coefficients of composite modulation code, $codeX =$ (Modulation code coefficients of modulation code, $code1$) ×

(Modulation code coefficients of modulation code, $code2$) =

-continued

{+1×(+1, +1, −1, +1), +1×(+1, +1, −1, +1), +1×(+1, +1, −1, +1),

−1×(+1, +1, −1, +1), +1×(+1, +1, −1, +1)} = {+1, +1, −1, +1,

+1, +1, −1, +1, +1, +1, −1, +1, −1, −1, +1, −1, +1, +1, −1, +1}

The code composing means 56 successively outputs signals representing the coefficients (+1 or −1) of the code elements of the generated composite modulation code, codeX, to the waveform selection means 32 with a predetermined time interval. Because the coefficients of the code elements of the composite modulation code, codeX, consists of two values (+1 or −1) in this embodiment, two kinds of waveforms corresponding to them, i.e., a fundamental waveform (phase 0°) and a waveform of which phase is shifted by 180° with respect to the fundamental waveform, are stored beforehand in the waveform storage means 26. The waveform selection means 32 distinguishes the coefficients of the code elements of the codeX on the basis of the signals successively received from the code composing means 56. When a coefficient of a received code element is +1, it directs the waveform storage means 26 to output the fundamental waveform, and when it is −1, it directs the waveform storage means 26 to output a waveform with a phase of 180°. The waveform storage means 26 successively outputs the directed waveforms to the wave transmission amplifier 28, and thus analog signals of a modulated waveform representing the coefficients of the composite modulation code, codeX, with phases are outputted to the wave transmission amplifier 28. The wave transmission amplifier 28 generates signals in which the modulated waveform representing codeX is amplified (called encoded driving signals), and outputs them to the delay circuit 11 for wave transmission shown in FIG. 1.

In accordance with directions from the controller 20, the delay circuit 11 for wave transmission delays the encoded driving signals with delays according to the positions of the oscillators to generate encoded driving signals and delivers them to the transmission/reception changing switches 13. The transmission/reception changing switches 13 supply the encoded driving signals with different delays to the oscillators at the positions specified by the controller 20. Ultrasonic beams modulated with codeX are thereby transmitted from the oscillators of the probe 10. Focusing at the time of wave transmission is realized by the aforementioned delays.

Ultrasonic waves reflected or scattered in the object are converted into reception signals by each of the oscillators of the probe 10, and delivered to the reception means 14 by the transmission/reception changing switches 13. Because the ultrasonic waves transmitted into the object are modulated by encoding, the reflected or scattered waves thereof are also modulated by encoding. Therefore, a decoding operation is performed by the reception means 14.

The configuration and operation of the reception means 14 will be specifically explained. The reception means 14 is provided with amplifiers 34, A/D converters 36, first demodulators 40, a phasing addition means 42, a second demodulator 44, and a signal processing means 46, as shown in FIG. 1. There are disposed amplifiers 34, the A/D converters 36 and the first demodulators 40 each in the same number as that of the oscillators of the probe 10. The amplifiers 34 amplify the reception signals of the oscillators by TGC (Time Gain Compensation) operation, respectively, and the A/D converters 36 convert the analog reception signals into digital signals. The first demodulators 40 perform the first stage demodulation that demodulates the encoding with the code1 for each reception signal. The phasing addition means 42 receives signals after the demodulation from all the first demodulators 40, and perform phasing and addition of the signals. Because the second demodulator 44 processes the reception signals bundled into one by phasing addition, a single second demodulator 44 is provided, and it performs the second stage demodulation that demodulates the encoding with code2 for the reception signals.

Figure 4:
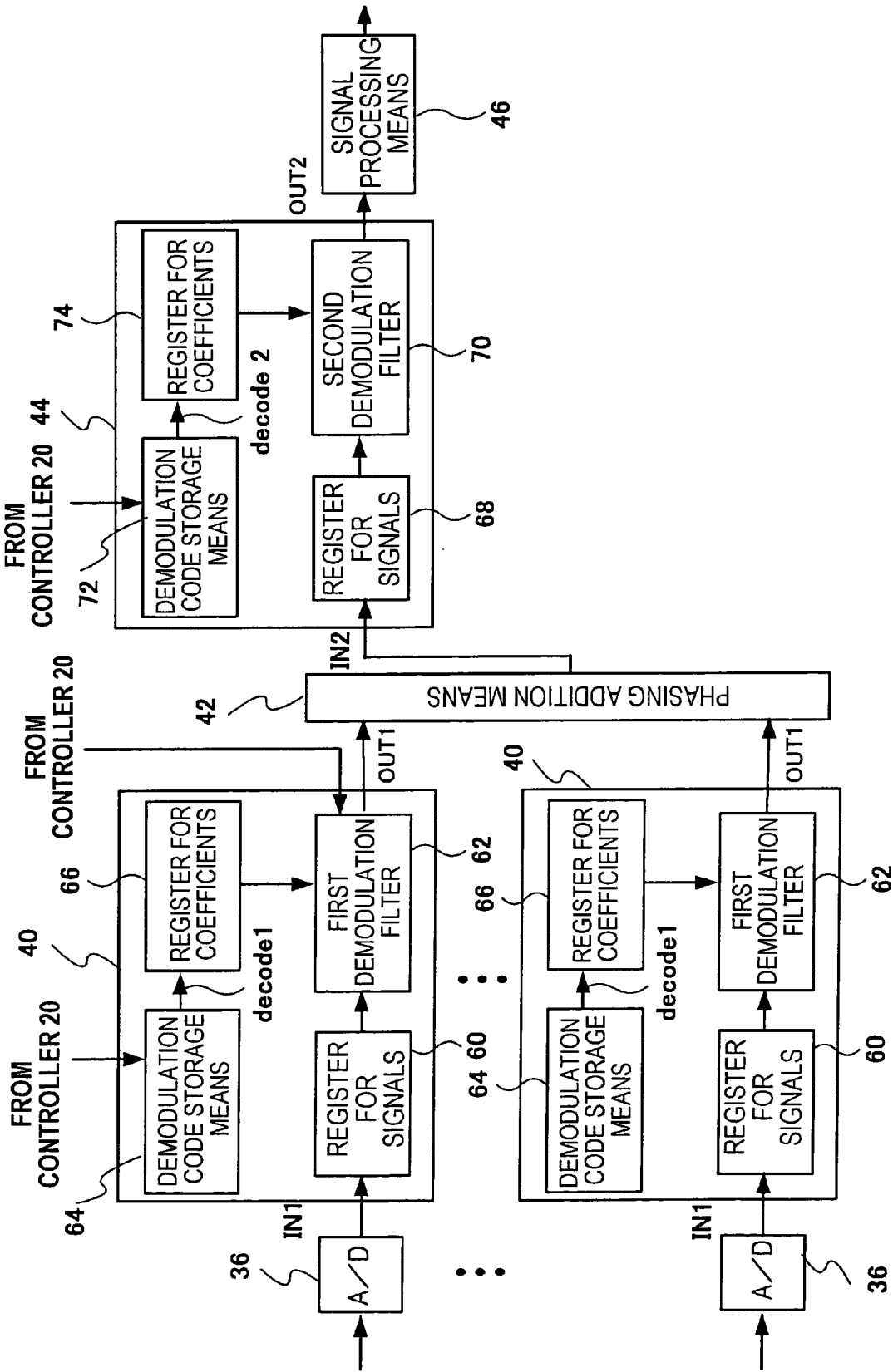
[FIG. 4]
Figure 5:
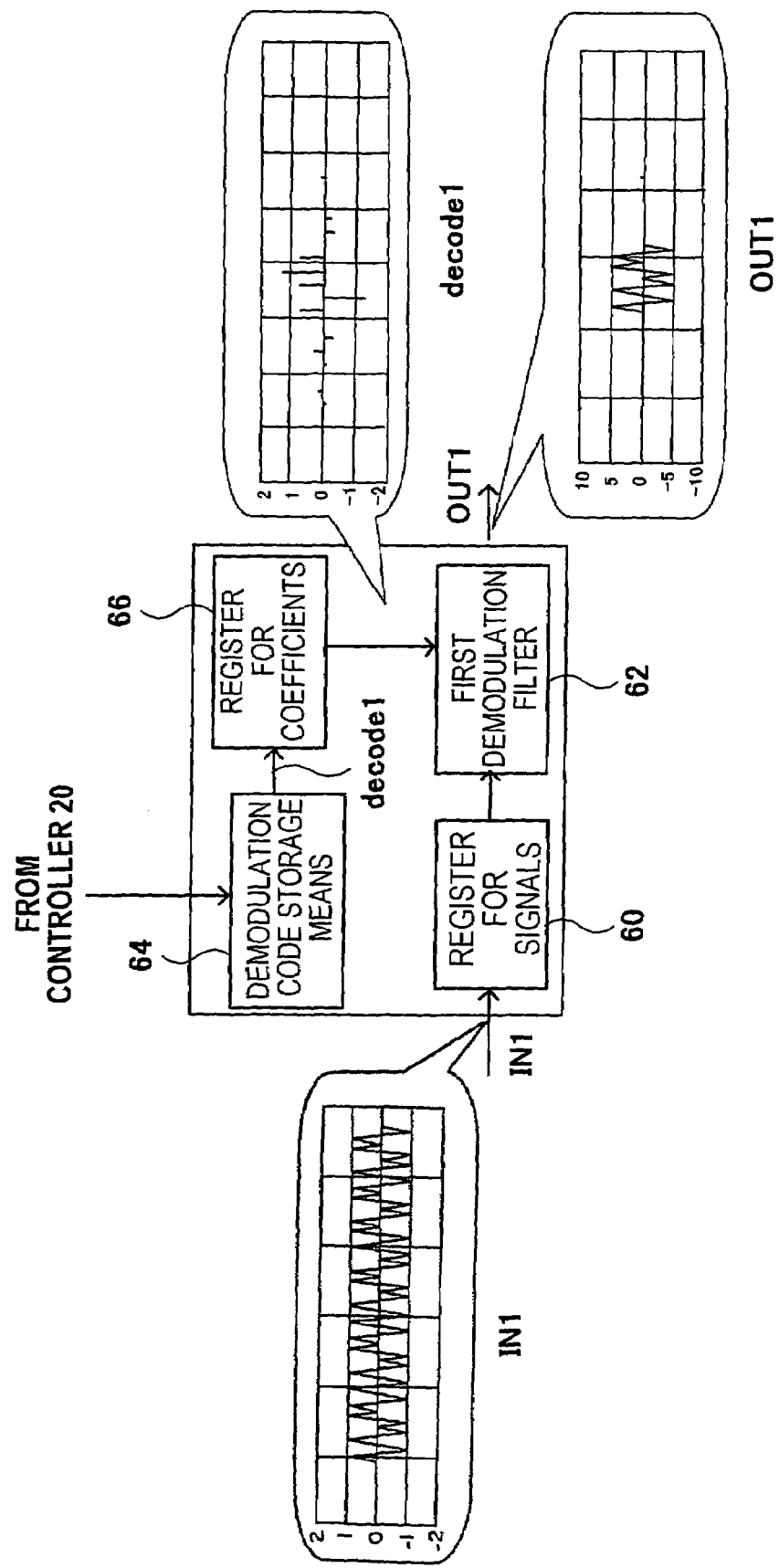
[FIG. 5]

Each first demodulator 40 is provided with a register 60 for signals, a demodulation code storage means 64, a register 66 for coefficients, and a first demodulation filter 62 as shown in FIG. 4. Demodulation operation conducted by these will be explained with reference to FIG. 5. The register 60 for signals retains reception signals (IN1) converted into digital signals by the A/D converter 36. Multiple decoding codes (decode1) corresponding to all the kinds of the modulation codes (code1) stored in the code storage means 51 of the transmission means 12 are stored beforehand in the demodulation code storage means 64. The demodulation code storage means 64 outputs decoding codes (decode1) of the kinds corresponding to the codes used as the code1 in the transmission means 12 to the register 66 for coefficients in accordance with a direction from the controller 20. The register 66 for coefficients retains decode1 outputted from the demodulation code storage means 64. The first demodulation filter 62 conducts product summing up operation for the code coefficients of the decode1 retained in the register 66 for coefficients and the values of the reception signals retained in the register 60 for signals in accordance with a direction of the controller 20 to demodulate the reception signals for the code1 and thereby provides signals (OUT1). The demodulation filter 62 is constituted by an FIR filter or the like, and such a filter of a required degree is prepared beforehand.

For example, when the code1 consists of Barker codes, either matched filter coefficients obtained by reversing the coefficients of the code1 for the time axis, mismatched filter coefficients of which amplitudes of coefficients are not 1, or deconvolution filter coefficients for obtaining a value near 1 by a convolution operation with code1 are used as decode1. The first demodulation filter 62 operates as a matched filter, a mismatched filter, or a deconvolution filter through an operation of code1 and decode1. When mismatched filter coefficients are used as decode1, a larger degree of decode1 (longer code length) can more reduce the time side lobe. Therefore, when Barker codes are used, a first demodulation filter 62 which can calculate decode1 of a degree providing a required time side lobe level (for example, 31st order) is prepared. When code1 consists of Golay codes, matched filter coefficients which are reversed coefficients of the code1 for the time axis are used as decode1, and the first demodulation filter 62 operates as a matched filter which executes a product summing up operation for these. Therefore, the degree required for the first demodulation filter 62 in the case of using Golay codes is the same as that of the code length (number of code elements), and for example, when Golay codes with a code length of 4 are used, the degree may be 4th order. Thus, depending on the kind of codes used as code1 and kind of decode1, operation performance required for the first demodulation filter 62 varies. Therefore, as the first demodulation filter 62, one having operation capacity for the maximum degree to be required depending on the kind of the codes stored beforehand in the code storage means 51 is provided. This makes demodulation by the first demodulator 40 possible irrespective of the codes chosen as code1.

As described above, the reception signals OUT1, of which encoding with code1 having a large code interval is demodulated by each first demodulator 40, are summed after the phases are delayed for predetermined different delay times by the phasing addition means 42 and thereby bundled into one reception signal. This realizes focusing at the time of wave reception. The encoding with code2 of the added reception signal has not been demodulated yet. Therefore, the encoding with code2 is demodulated by the second demodulator 44.

The second demodulator 44 has the same configuration as the first demodulator 40 as shown in FIG. 4, and is provided with a register 68 for signals, a demodulation code storage means 72, a register 74 for coefficients, and a second demodulation filter 70. The decoding operation executed by the second demodulator 44 will be explained with reference to FIG. 6. In the demodulation code storage means 72, decoding codes (decode2) each corresponding to all the kinds of the modulation codes (code2) stored in the code storage means 50 are stored beforehand. The demodulation code storage means 72 outputs decode2 corresponding to code2 chosen in the transmission means 12 to the register 74 for coefficients in accordance with a direction from the controller 20. Decode2 is thereby retained by the register 74 for coefficients. The second demodulation filter 70 demodulates the output signals of the phasing addition means 42 retained by the register 68 for signals by a product summing up operation with the coefficients of decode2 retained by the register 74 for coefficients to provide demodulated reception signals (OUT2). All the encoded modulations of the reception signals are thereby demodulated, thus energy of the reception signals is converged along the time axis direction, and the reception signals are made into short pulse signals having amplitudes reflecting the reflection intensities of the object. The second demodulation filter 70 operates in the demodulation operation in the same manner as that of the first demodulation filter 62. Further, the second demodulation filter 70 has a operation performance for the maximum degree required depending on the kind of code2.

The reception signals demodulated in two steps by the reception means 14 as described above are sent to the signal processing means 46, and subjected to a predetermined signal processing directed by the controller 20 as required. For example, when complementation type codes such as the Golay codes are used for at least either one of code1 and code2, reception signals obtained by performing transmission and reception more than twice with inverse codes are added. Short pulse signals having amplitudes reflecting reflection intensities of an object are thereby obtained. The configuration and operation of the reception means 14 are as described above. The image reconstruction means 16 reconstitutes an ultrasonogram (for example, B-mode image, M-mode image etc.) by performing signal processed image reconstruction, and displays it on the display 18.

Figure 6:
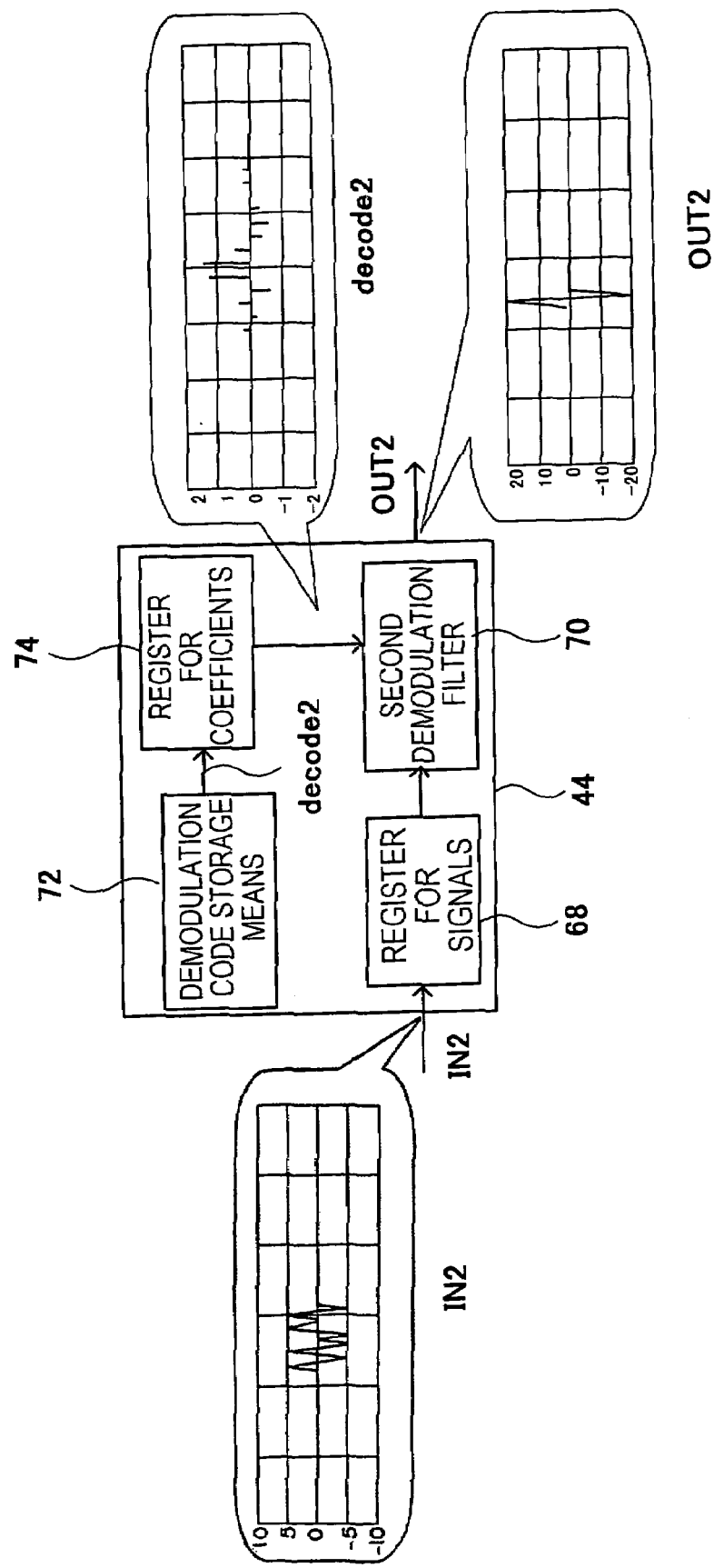
[FIG. 6]

Although not illustrated in the reception signals (OUT2) shown in FIG. 6, in the encoded transmission/reception techniques, undesired signals called time side lobe are generated before and after signals originally desired to be obtained, when energies of reception signals are converged along the time axis direction. The ultrasonic diagnostic apparatus of this embodiment provides the first advantage that the time side lobe can be reduced without increasing the circuit scale. Moreover, it also provides the second advantage that demodulation errors accompanying the focal stage change in the dynamic focus can be prevented.

Figure 7:
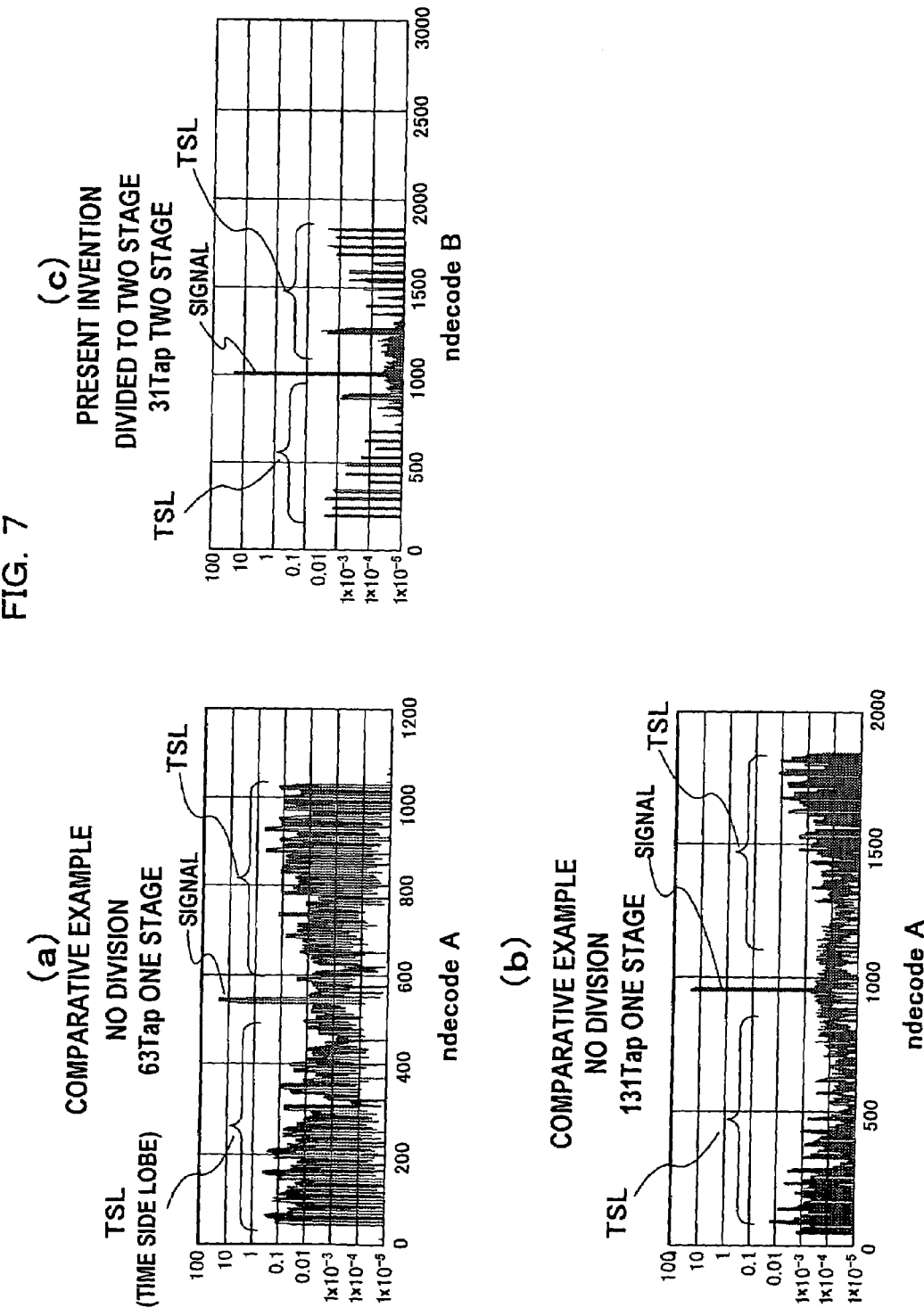
[FIG. 7]

First, the first advantage will be explained with reference to FIGS. 7(*a*) to 7(*c*). FIG. 7(*a*) and 7(*b*) show waveforms of reception signals after demodulation performed as batch demodulation only with the first demodulator 40 without using the second demodulator 44 used in the configuration of FIG. 1 as comparative examples. In FIG. 7(*a*), a mismatched filter with a degree (number of taps) of 63 is used as the demodulation filter 62 of the first demodulator 40, and in FIG. 7(*b*), a mismatched filter of 131 taps is used as the same. As the decoding codes for transmission signals, codeX having a code length of 20 composed from Barker codes of a code length 4 and code length 5 shown in FIG. 3 is used, and as the decoding codes, decode1, used in the demodulation filter 62 of the comparative examples, one enabling one step demodulation of codeX is used.

In the case of the comparative example using the mismatched filter of 63 taps, the signal level of the time side lobe is about 0.5 dB as shown in FIG. 7(*a*), and thus the signal level of the time side lobe is comparatively large. In the case of the comparative example using the mismatched filter of 131 taps, the signal level of the time side lobe is reduced to about 0.02 dB as shown in FIG. 7(*b*). From these two comparative examples, it can be seen that the signal level of the time side lobe can be suppressed by increasing the number of taps of the demodulation filter. However, the demodulation filter requires operation circuits of the same number as the tap number, and therefore if the number of the oscillators of the probe 10 is k in the comparative example using the demodulation filter of 131 taps, 131×k of operation circuits are required, and thus the circuit scale increases.

On the other hand, in the first embodiment of the present invention, by using the composite modulation code, codeX, composed from the modulation codes, code2 and code1, demodulation can be attained by divided two stages, i.e., by the first demodulator 40 and the second demodulator 44. Therefore, even if the mismatched filter consisting of the first and second demodulation filters 62 and 70 each of 31 taps is used, the signal level of the time side lobe is about 0.03 dB as the waveform of the reception signal after the demodulation is shown in FIG. 7(*c*), and thus there is obtained a time side lobe reduction effect (rejection effect) more than equivalent to that obtained in the case of FIG. 7(*b*). In addition, the numbers of operation circuits are 31×k for the first demodulation filter 62 and 31 for the second demodulation filter 70, and thus the number of operation circuits of the filter is (31×k)+31 in total. Therefore, compared with the comparative example using the filter of 131 taps (circuit number is 131×k), more than equivalent time side lobe reduction effect can be obtained with a number of operation circuits below half of that of the comparative example. Thus, in this embodiment, a circuit scale can be made smaller compared with the case of performing the demodulation operation as a batch in one step while maintaining the rejection level of time side lobe at a desired level.

This first advantage is not limited to a case of using Barker codes as the modulation code, and it is similarly obtained for a case of using, for example, Golay codes. For example, if the code length of the modulation code is 64, a 64th order matched filter is required for demodulation with one stage of demodulation filter, and operation circuits in a number of 64×k are required. However, even in the case of using codes having the same code length of 64, if the modulation code, codeX, composed from codes each having a code length of 8 is used, 8th order matched filters can be used as the demodulation filters 62 and 70, and the demodulation can be attained with operation circuits in a number of (8×k)+8. Therefore, the circuit scale can be reduced to about ¼.

Figure 8:
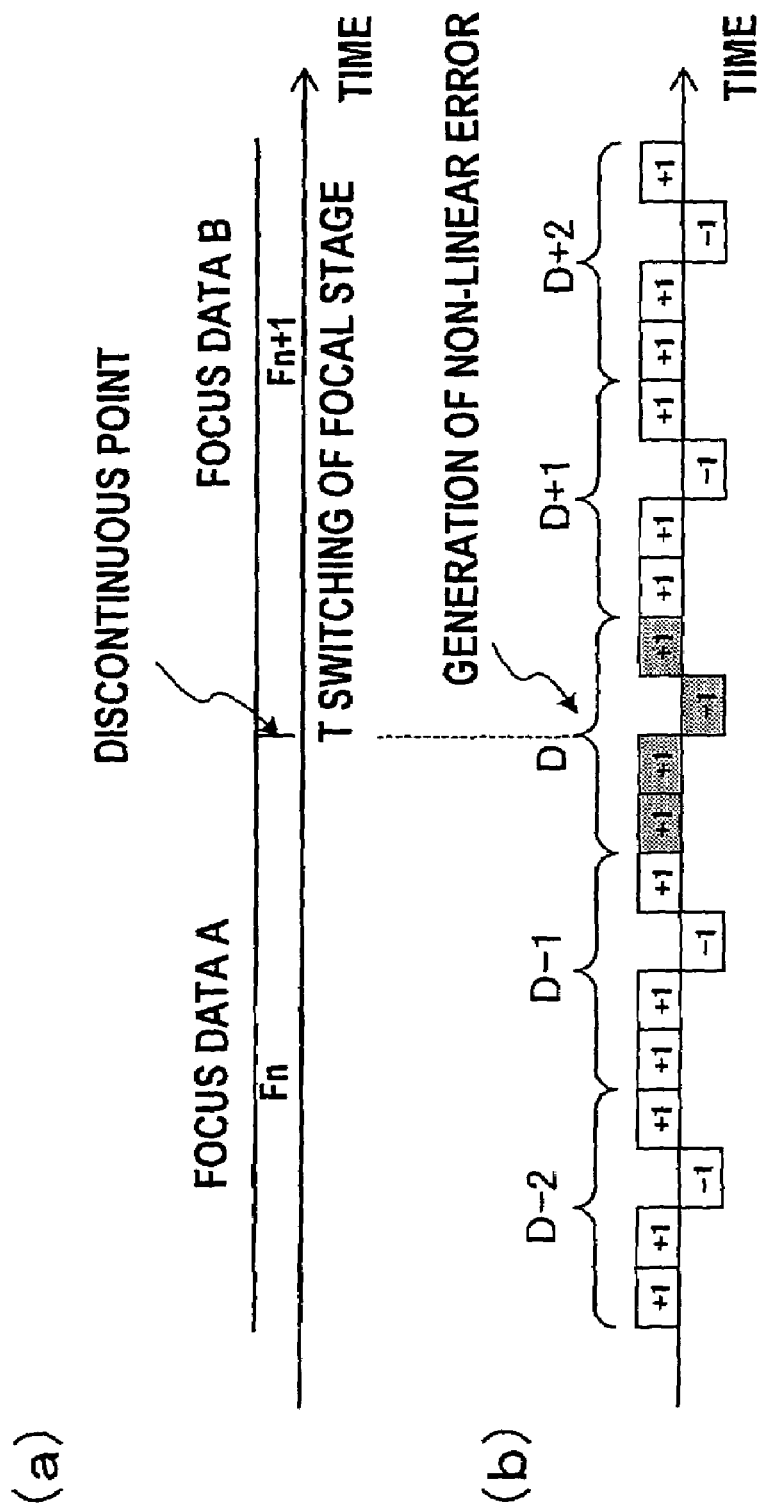
[FIG. 8]

Hereafter, the second advantage of the prevention of demodulation errors accompanying the focal stage change in the dynamic focus will be explained. In the ultrasonic diagnostic apparatus of this embodiment, a dynamic focus processing function known as a focusing technique at the time of reception is provided in the phasing addition means 42 in order to improve image resolution. In the dynamic focus technique, multiple sampling points (reflection sources) designated along the depth direction of an object are grouped into multiple focal stages, and focal data are commonly set up for every focal stage. By using these focal data to perform phasing of the reception signals in the phasing addition means 42, it becomes possible to converge ultrasonic beams at the time of wave reception in a comparatively wide range along the depth direction. The focal data are switched for every change of the focal stage. Specifically, as shown in FIG. 8(*a*), the phasing addition means 42 carries out phasing of the reception signals by using the focal data A in the focal stage Fn, and at a set period T, it switches the focal stage to Fn+1 which uses the focal data B.

If an encoded transmission/reception technique is employed in an ultrasonic diagnostic apparatus which performs such a dynamic focus operation, and the demodulation is performed after the phasing addition, the focal stage switching operation may be performed in the middle of a reception signal wave corresponding to one code element of a reception signal. For example, if a transmission waveform is modulated with the composite modulation code, codeX, shown in FIG. 3, such an encoded reception signal as shown in FIG. 8(*b*) is obtained. This reception signal is modulated with the code elements D−2, . . . D, . . . D+2 of code1 having long code intervals and code elements corresponding to code2 which further encodes the foregoing code elements. If the focal stage is switched in the middle of a reception signal wave of one code element D among such coding reception signals, the first half of the code element D belongs to the processing time of the focal stage Fn, whereas the second half belongs to the processing time of the focal stage Fn+1. Thus, the phasing is carried out with different focal data, and therefore the reception signal waveform of the code element D becomes discontinuous at the time T. Therefore, the demodulation operation of the code element D is no longer correctly performed, and such time side lobe as shown in FIG. 9(*a*) is generated in the demodulated signal due to the generated error. This phenomenon appears more notably for a longer code length constituting a code element for which a demodulation error is caused.

On the other hand, in this embodiment, the first demodulator 40 and the second demodulator 44 are disposed before and after the phasing addition means 42, the modulation code, code1, with a large code interval (time length between code elements) is demodulated before the phasing addition means 42, and the modulation code with a small code interval, code2, is demodulated after the phasing addition means 42. Therefore, the code elements with a large code interval are already demodulated before being inputted into the phasing means 42, and thus the discontinuous operation due to the focal stage switching at the time of phasing is not executed in the middle of a code element with a large code interval. Therefore, the time side lobe can be reduced. Although a focal stage change may occur in the middle of the code with a small code interval, code2, the number of code element for which the error occurs is only one element of code2, and the time side lobe produced by it is small.

In this embodiment, the time side lobe originating in the discontinuous operation of the switching of the focal stage is reduced by disposing the first demodulator 40 and the second demodulator 44 before and after the phasing addition means 44. However, in an ultrasonic diagnostic apparatus, discontinuous operations also occur due to the aperture switching operation in variable aperture selection means incorporated in the transmission/reception changing switches 13, switching of the amplification factor of the TGC operation performed by the amplifier 34 and so forth. When the level of the time side lobe of the demodulation error caused by these is large, it is possible to dispose the demodulators 40 and 44 before and after the positions of these operations. That is, by disposing the first demodulator 40 and the second demodulator 44 before and after the variable aperture selection means or the amplifier 34, the time side lobe of demodulation error produced by a discontinuous reception waveform due to the aperture switching operation or demodulation error produced by a discontinuous reception waveform due to the TGC amplification factor switching operation can be reduced. In addition, when the first and second demodulators 40 and 44 are disposed before the A/D converter 36, demodulators for analog signals are used.

Although the first embodiment is explained above, the present invention is not limited to the configuration of the first embodiment. For example, although an example in which the composite modulation code, codeX, is composed from two kinds of modulation codes, code1 and code2, is explained for the first embodiment, it is also possible to synthesize three or more codes to obtain a composite modulation code. In such a case, code elements of the first modulation code can be modulated with the second modulation code among the multiple modulation codes to form a composite modulation code, and code elements of the formed composite modulation code can be modulated with another modulation code according to a direction from the controller 20.

Further, although the phasing addition is performed by one step in the phasing means 42 in the first embodiment, it is also possible to divide the oscillators (output channels) constituting the probe 10 into two or more groups, perform phasing addition of the reception signals in the first phasing addition means disposed for every group, and carry out phasing addition of all the outputs of the first phasing addition means in the second phasing addition means. This technique is described in, for example, Japanese Patent Unexamined Publication (KOKAI) No. 2003-225237. In this case, the first demodulator 40 can be disposed after each first phasing addition means, and the second demodulator 44 can be disposed after the second phasing addition means. The number of the first demodulators 40 can be thereby reduced compared with the configuration of FIG. 1, and therefore the circuit scale can be further reduced.

Types of the codes of the first and second modulation codes, code1 and code2, can be suitably chosen according to characteristics of imaging portion, diagnosis items, number of operation circuits which can be disposed in the imaging apparatuses and so forth. Code1 and code2 may consist of codes of different kinds. For example, although code2 shown in FIG. 3 was used as Barker codes in the above explanation, this code sequence is the same as the Golay codes with a code length of 4, and therefore it can also be used as Golay codes. In this case, codeX is a composite code of code1 of Barker codes and code2 of Golay codes. Therefore, codes corresponding to code2 inversed for the time axis are used as decode2 in the second demodulator that demodulates code2 so that the second demodulation filter 70 should operate as a demodulation filter for Golay codes.

For complementary type codes such as Golay codes, it is necessary to repeat transmission and reception more than twice. However, the degree of the demodulation filter becomes comparatively small, and therefore when they are used as the codes, code1, which are demodulated in the first demodulator 40 required in the same number as that of the oscillators, the operation circuit scale of the whole apparatus can be effectively reduced. On the other hand, since Barker codes and Chirp codes have a characteristic that information can be extracted from inspection site including a moving object such as blood flow, contrast agent or the like by one transmission and reception, they are suitable for short time imaging. By combining different kinds of multiple codes, advantages of the modulation codes can be properly used depending on the characteristics of an imaging portion, and at the same time, the time side lobe can be reduced with reducing the circuit scale.

As explained above, a composite modulation code generated from usual codes such as Barker codes, Golay codes and Chirp code is used in this embodiment. However, the characteristic of the present invention resides in that the composite modulation code is not a code obtained by simply combining usual codes, but a code obtained by composing two or more codes. That is, by modulating each code element of one code with all the code elements of the other code, it is made possible to simultaneously obtain the first advantage of the reduction of circuit scale and the second advantage of the reduction of time side lobe described above.

Second Embodiment

The ultrasonic diagnostic apparatus according to the second embodiment of the present invention will be explained with reference to FIG. 10. In the ultrasonic diagnostic apparatus of the second embodiment, the first demodulator 40 is disposed after the phasing addition means 42. The configuration other than this is the same as that of the first embodiment.

Figure 10:
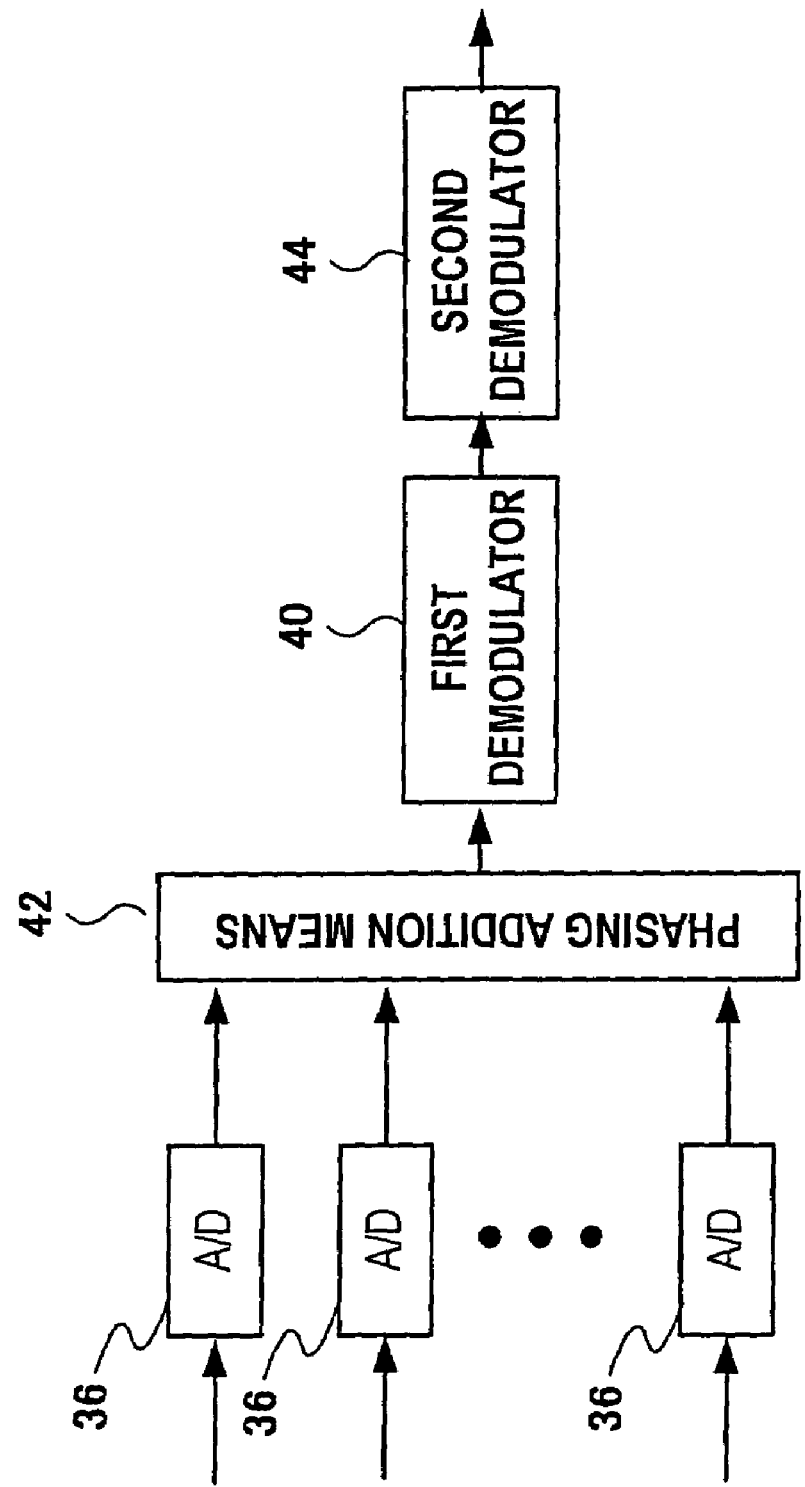
[FIG. 10]

The configuration shown in FIG. 10 in which the first demodulator 40 is disposed after the phasing addition means 42 does not provide the second advantage of the reduction of the time side lobe accompanying the focal stage switching explained for the first embodiment, but sufficiently provides the first advantage of the reduction of the circuit scale with reducing the time side lobe at the time of demodulation. This is because as follows. Because the first demodulator 40 is disposed after the phasing addition means 42, it is not necessary to dispose the first demodulator 40 for every oscillator of the probe 10. Therefore, only one first demodulator 40 is sufficient as is the second demodulator 44, and thus the circuit scale is further reduced compared with the configuration of the first embodiment. In addition, because the two-step configuration of the first demodulator 40 and the second demodulator 44 is employed, the circuit scale for one demodulation device is reduced compared with the conventional one-step configuration. For example, in a comparative example where a demodulator of one-step configuration is disposed after the phasing addition means 42 like the configuration shown in FIG. 7(b), it is necessary to use a demodulation filter of 131 taps. However, if the two-step configuration of the demodulators 40 and 44 is used as in the second embodiment, the time side lobe can be reduced with two steps of 31 taps as in FIG. 7(c) to a level less than equivalent to the level obtained with one step of 131 taps. The operation circuit number for two steps of 31 taps is 31×2=62. Therefore, the time side lobe reduction effect more than equivalent to that obtained with one step of 131 taps can be obtained with an approximately half operation circuit scale.

Because both the first and second demodulators 40 and 44 are disposed behind the phasing addition means 42, either of the first and second demodulators 40 and 44 may precede the other. The second demodulator 44 may be disposed in the phasing addition means 42, and the first demodulator 40 may be disposed behind that.

Third Embodiment

The ultrasonic diagnostic apparatus according to the third embodiment of the present invention will be explained with reference to FIG. 11. In the ultrasonic diagnostic apparatus of the third embodiment, the second demodulator 44 is disposed before the phasing addition means 42. The configuration other than this is the same as that of the first embodiment.

Figure 11:
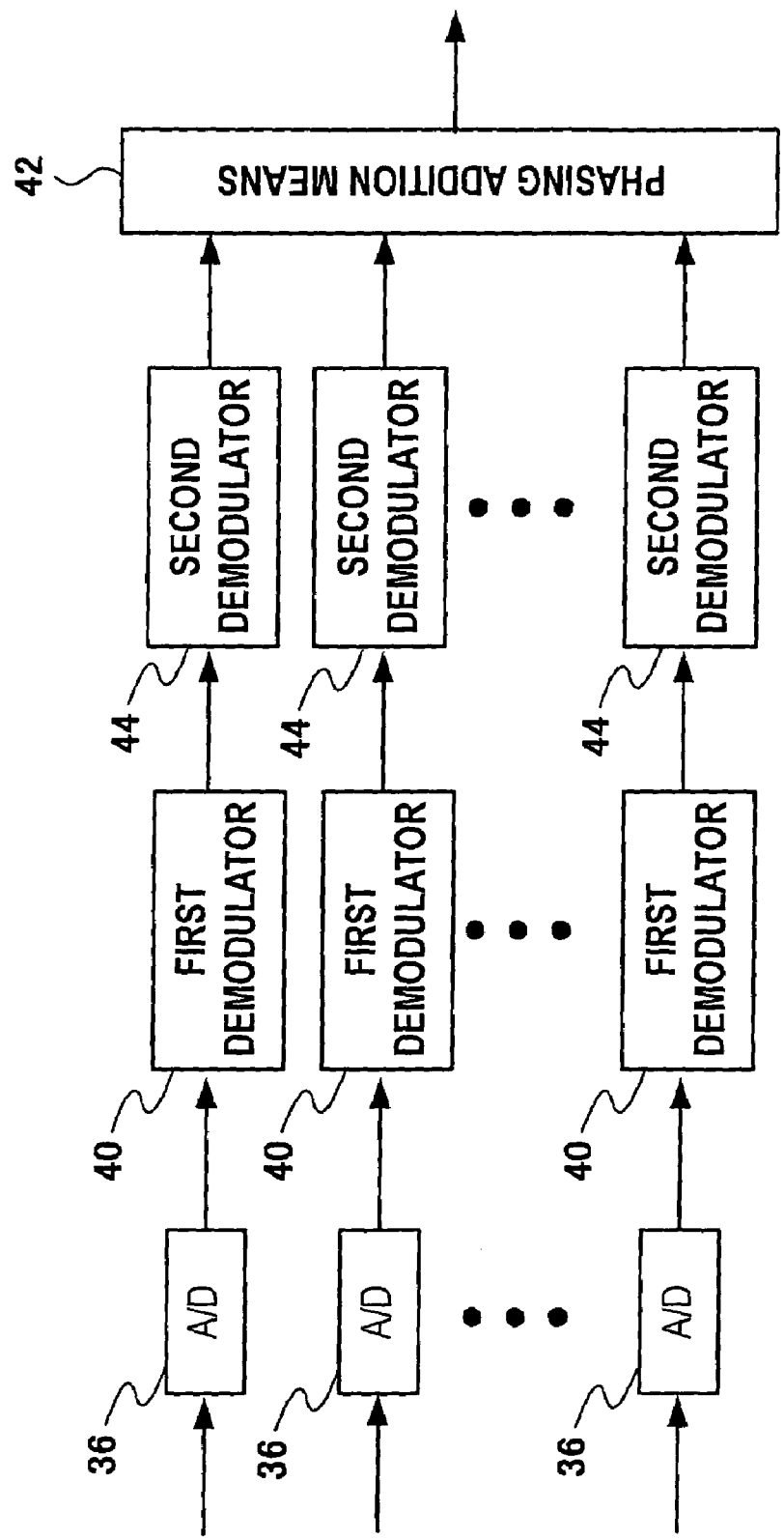
[FIG. 11]

In the configuration of FIG. 11 where the second demodulators 44 as well as the first demodulators 40 are disposed before the phasing addition means 42, demodulation of reception signals is completed before phasing addition. Therefore, there is obtained an advantage that the time side lobe due to the demodulation error accompanying the focal stage switching explained for the first embodiment does not occur. On the other hand, because it is necessary to dispose the second demodulator 44 in the same number as the oscillators of the probe 10, the advantage of circuit scale reduction becomes smaller compared with the first and second embodiments. However, the advantage can be sufficiently obtained compared with the case of disposing a demodulator of one-step configuration before the phasing addition means 42 as in conventional techniques. The reason is as follows. In a comparative example where a demodulator of one-step configuration is disposed behind the phasing addition means 42, it is necessary to use a demodulation filter of 131 taps as in the configuration shown in FIG. 7(b). Therefore, if the number of oscillators is k, 131×k of operation circuits are required. However, if the two-step configuration is used as shown in FIG. 11, the time side lobe can be reduced with two steps of 31 taps to a level less than equivalent to the level obtained with one step of 131 taps as in FIG. 7(c). The operation circuit number of two steps of 31 taps may be 31×k×2=62. Therefore, the time side lobe reduction effect more than equivalent to that obtained with one step of 131 taps can be obtained even with an approximately half operation circuit scale.

Because both the first and second demodulators 40 and 44 are disposed before the phasing addition means 42, either of the first and second demodulators 40 and 44 may precede the other. The second demodulator 44 may be disposed behind the probe 10, and the first demodulator 40 may be disposed behind that.

Fourth Embodiment

Figure 12:
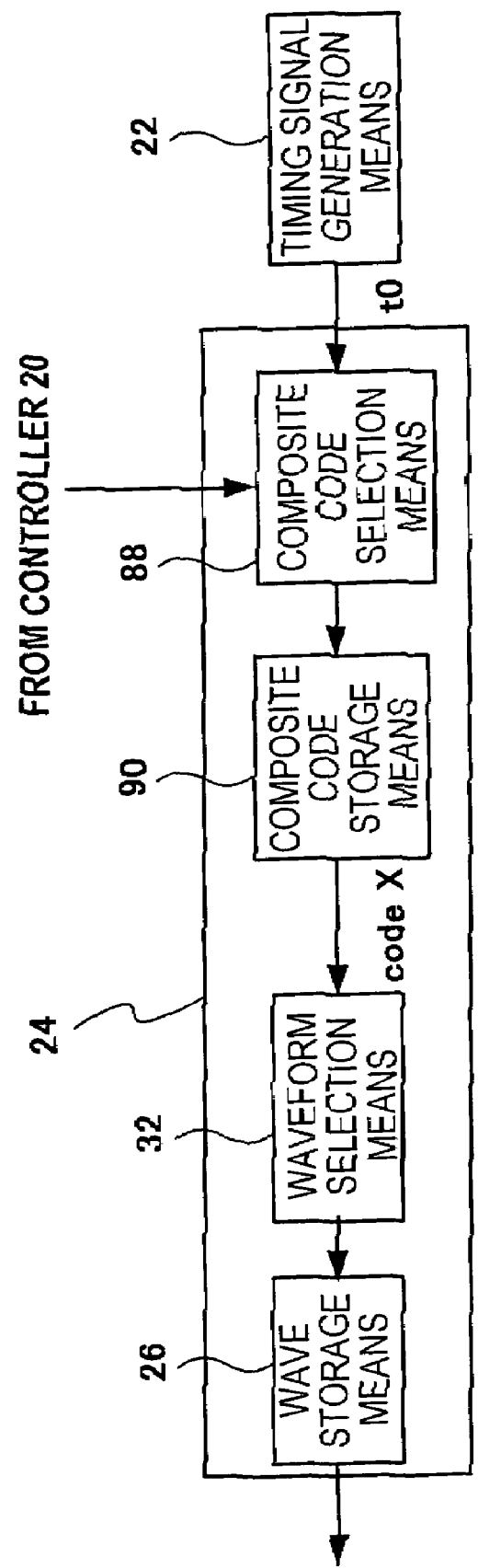
[FIG. 12]

The ultrasonic diagnostic apparatus according to the fourth embodiment of the present invention will be explained with reference to FIG. 12. The configuration shown in FIG. 12 is different from that of the first embodiment in that a composite code storage means 90 is disposed in the transmission waveform generation means 24, and multiple composite modulation codes each composed from two kinds of modulation codes, code1 and code2, are stored therein beforehand. A composite code selection means 88 chooses one composite modulation code, codeX, among them according to a control signal from the controller 20. The selected codeX is received by the waveform selection means 32. To the first demodulator 40 and the second demodulator 44, control signals for selecting decode1 and decode2 corresponding to code1 and code2 constituting the selected codeX are outputted from the controller 20. The other configuration is the same as that of the first embodiment.

According to the fourth embodiment, the configuration for generating the composite modulation code becomes simpler compared with that of the first embodiment, and therefore the circuit scale can be made smaller. Moreover, because multiple kinds of composite modulation codes are stored in the synthetic demodulation code storage means 90, it becomes easy to select a composite modulation code suitable for characteristics of an imaging portion, and therefore the user-friendliness of the apparatus can be improved. In addition, this embodiment can be suitably combined with the second and third embodiments.

Fifth Embodiment

The ultrasonic diagnostic apparatus according to the fifth embodiment of the present invention will be explained with reference to FIGS. 13(*a*), 13(*b*) to 16. In order to improve the image resolution of ultrasonograms of living body tissues and blood flows, the contrast echo method, tissue harmonic imaging method and so forth are performed. The contrast echo method is a technique of administering an ultrasonic contrast agent to an object, and reconstructing an ultrasonogram on the basis of harmonic components (for example, secondary harmonics, third harmonics etc.) of ultrasonic waves reflected by microbubbles of the administered ultrasonic contrast agent. The tissue harmonic imaging method is a technique of directing attentions to the fact that when an ultrasonic wave propagates in a living body as a compressional wave, distortion of the ultrasonic waveform is caused by sound pressure change due to sound pressure difference, and reconstructing an ultrasonogram on the basis of harmonic components resulting from the caused waveform distortion. In such contrast echo method and tissue harmonic imaging method, a distinctive ultrasonogram based on harmonic components can be reconstructed by using an imaging method for emphasizing harmonic components. In this embodiment, harmonic components of reception signals can be emphasized by applying the technique of using composite modulation codes explained in the first to fourth embodiments. Explanation will be made hereafter by exemplifying a case of emphasizing secondary harmonics of reflected signals.

Figure 13:
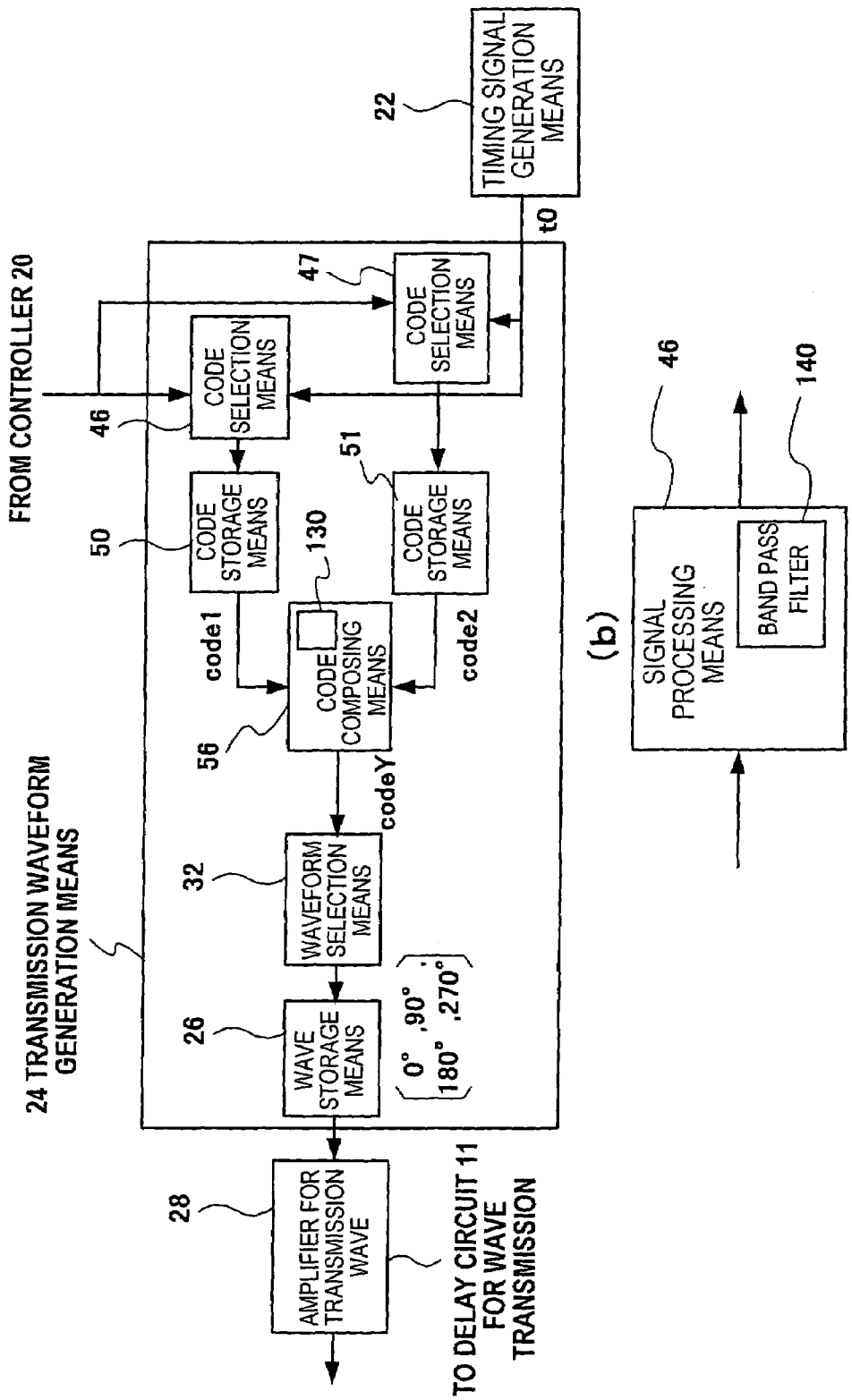
[FIG. 13]

Although the ultrasonic diagnostic apparatus of this embodiment fundamentally has the same configuration as that of the ultrasonic diagnostic apparatus of the first embodiment, as shown in FIG. 13(*a*), it is different from the first embodiment in that a phase modulation means 130 is provided in a code composing means 56 of the transmission waveform generation means 24, and at least three kinds of waveforms of 0°, 90° and 180° are stored in the waveform storage means 26 beforehand. Moreover, it is different from the first embodiment in that, as shown in FIG. 13(*b*), a band control filter (for example, bandpass filter) 140 which passes signals of desired frequency band of harmonics and cuts the other frequency bands is incorporated in a signal processing means 46 of the reception means 14. A phase modulation means 130 determines phase shift amounts with respect to the fundamental wave for each code element of the composite modulation code, codeX, which is composed by the code composing means 56 in the same manner as that of the first embodiment, and performs an operation of generating codeY represented by the phase shift amounts. According to the phase shift amounts of the code elements of this phase-shifted codeY, three kinds of waveforms of the waveform storage means 26 are chosen. Further, the band control filter 140 of the signal processing means 46 passes the frequency of the harmonics (secondary harmonics) desired to be emphasized, and attenuates and cuts the fundamental waves.

The operation of the code composing means 56 will be explained. As shown in FIG. 14, the code composing means 56 first multiplies the coefficients of code2 and the coefficients of code1 as in the first embodiment to generate the composite modulation code, codeX. The coefficients of the modulation code, codeX, are as follows.

<Modulation Code Coefficients of Composite Modulation Code, CodeX>

$$\text{Modulation code coefficients of composite modulation code, code} X =$$
$$(\text{Modulation code coefficients of modulation code, code1}) \times$$
$$(\text{Modulation code coefficients of modulation code, code 2}) =$$
$$\{+1 \times (+1, +1, -1, +1), +1 \times (+1, +1, -1, +1), +1 \times (+1, +1, -1, +1),$$
$$-1 \times (+1, +1, -1, +1), +1 \times (+1, +1, -1, +1)\} =$$
$$\{+1, +1, -1, +1, +1, +1, -1, +1, +1, +1, -1,$$
$$+1, -1, -1, (-1)^2, -1, +1, +1, -1, +1\}$$

The phase modulation means 130 counts, for each code element of the composite modulation code, codeX, the total (degree) of the negative coefficients of the coefficients of the modulation code, code2, and the negative coefficients of the coefficients of the modulation code, code1, multiplied to obtain the code element. That is, for every code element of codeX, the multiplication degree of "negative polarity (−1)" is counted at the time of the synthesis. For example, when the coefficient of code2 is +1, and the coefficient of code1 is +1, the degree of the code element of the coefficient +1 of codeX, which is obtained by multiplying them, is 0. When the coefficient of code2 is +1, and the coefficient of code1 is −1, the code element of −1 of codeX obtained from them is obtained by multiplying −1 once, and therefore the degree thereof is 1. When the coefficient of code2 is −1, and the coefficient of code1 is −1, the code element of +1 of codeX obtained from them is obtained by multiplying −1 twice, and therefore the degree thereof is 2.

Figure 15:
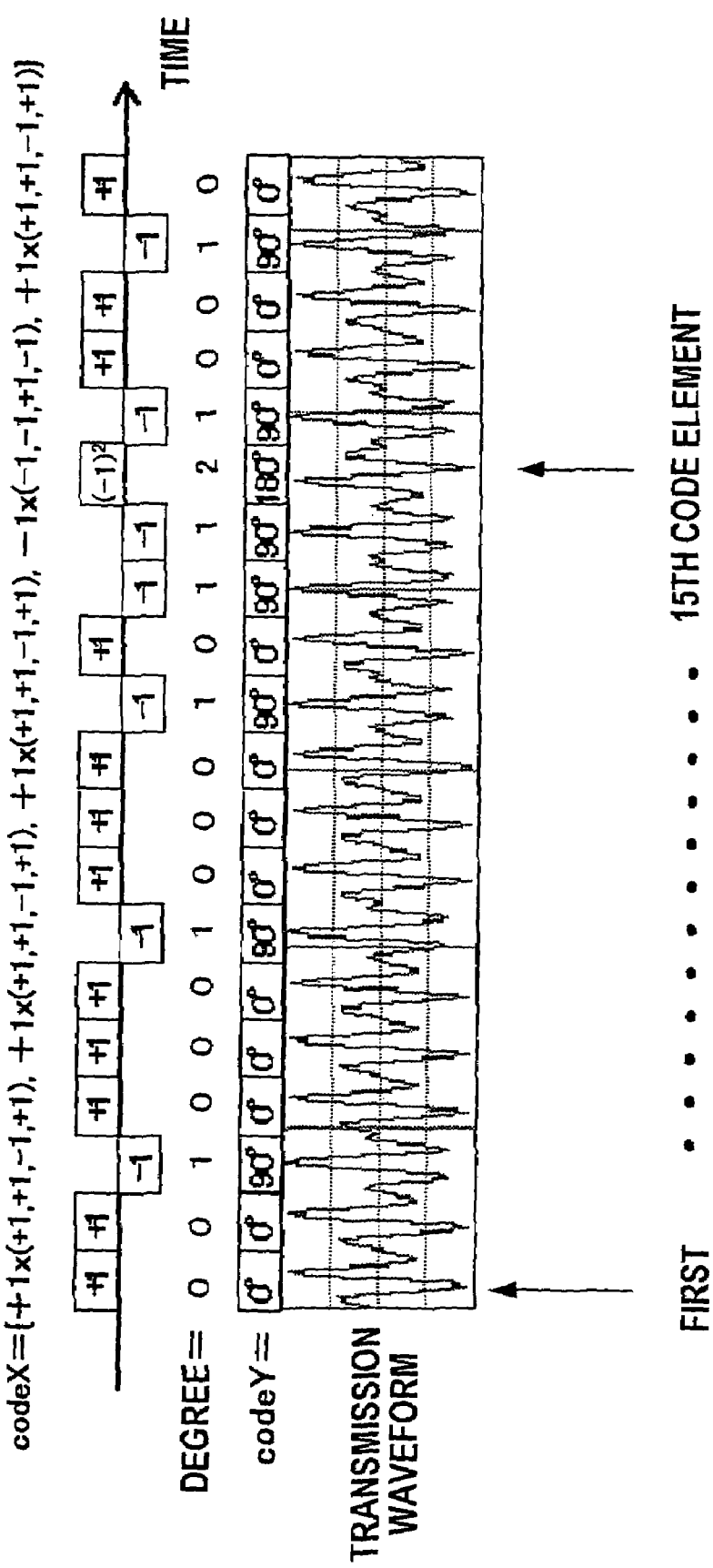
[FIG. 15]

Therefore, as shown for each code element of the composite modulation code, codeX, in FIG. 15, the degrees of the first and the second code elements are 0. The degree of the third code element is 1. The degree of the fourth code element is 0. The degree of the 15th code element is 2, because −1 is multiplied twice.

The phase modulation means 130 determines amounts of phase shift with respect to the fundamental wave for each code element of the composite modulation code, codeX, according to the counted degrees, and generates codeY represented by amounts of phase shift. The fundamental wave is assigned to a degree of 0, phase shift of 90° is assigned to a degree of 1, and phase shift of 180° is assigned to a degree of 2. Thus, as shown in FIG. 15, because degrees of the first and the second code elements of the composite modulation code, codeY, are 0, 0° is assigned to them. Because the degree of the third code element is 1, 90° is assigned. The degree of the fourth code element is 0, 0° is assigned. For the other code elements, phase shift amounts are similarly determined according to the degrees. For the 15th code element, 180° is assigned, because the degree is 2. The phase shift amounts of the code elements of the composite modulation code, codeY, obtained as described above are as follows.

<Phases of Code Elements of Composite Modulation Code, CodeY>
{0°, 0°, 90°, 0°, 0°, 0°, 90°, 0°, 0°, 0°, 90°, 0°, 90°, 90°, 180°, 90°, 0°, 0°, 0°, 0°}

In the waveform storage means 26, a fundamental wave corresponding to 0°, and waveforms with the phase shift amounts of 90°, 180° and 270° are stored beforehand as shown in FIG. 16. The waveform selection means 32 makes the waveform storage means 26 output a waveform corresponding to the phase shift amount for every code element of codeY.

Operation of the encoded transmission and reception using such a composite modulation code, codeY, will be explained by exemplifying a case of administering an ultrasonic contrast agent. First, an ultrasonic contrast agent is administered to an object. Then, transmission signals for the waveform of the composite modulation code, codeY, are supplied from the transmission means 12 to the probe 10. Encoded ultrasonic beams are thereby transmitted from the probe 10. Encoded reflection echo signals reflected by microbubbles of the ultrasonic contrast agent are received by the probe 10. Because the reception signals outputted from the probe 10 is modulated with codeY, they are demodulated by the first demodulator 40 and the second demodulator 44. The demodulation codes used at this time are decode1 and decode2 corresponding to code1 and code2, respectively, which constitute the composite modulation code, codeX, as in the first embodiment. That is, code1 is demodulated by the first demodulator 40 using decode1, and code2 is demodulated by the second demodulator 44 using decode2.

By demodulating the waveform of codeY, which corresponds to codeX of which phase is shifted according to the multiplication degree of −1, in the same manner as that at time of demodulating codeX, there are obtained reception signals of which second harmonics are emphasized. Because these reception signals also contain the fundamental wave in the demodulated state, the second harmonic components are further emphasized by attenuating the fundamental wave with a frequency control filter 140 in the signal processing means 46. In this operation, since the second harmonics are emphasized, they can be easily separated from the fundamental wave, and secondary harmonics with a high SN ratio can be obtained. Therefore, by reconstituting an ultrasonogram on the basis of the obtained secondary harmonic components in the image reconstruction means 16, the image resolution of the ultrasonogram can be improved.

In the explanation of this embodiment, the case of emphasizing secondary harmonics is explained, and therefore the phase is shifted for each code element of the composite modulation code, codeX, by 90° for each time with respect to the fundamental wave according to the degree of (−1). However, not only the secondary harmonics, but third or higher harmonics can also be emphasized. For example, when third harmonics are emphasized, the phase can be shifted by a unit of 60° according to the degree, and when fourth harmonics are emphasized, the phase can be shifted by a unit of 45° according to the degree. In summary, when Mth harmonic components (M is an integer of 2 or more) of reflective echo signals are emphasized, phases of code elements of the composite modulation code are shifted by (180°/M)×N, wherein N is a degree of (−1) of each code element (N is an integer) with respect to the fundamental wave. At the same time, a band control filter 140 which passes the frequency band of the Mth harmonic components (M is an integer of 2 or more) and cuts the other bands is used as the band control filter 140 of the signal processing means 46.

In this embodiment, since the composite modulation code, codeX, is composed from two codes, code1 and code2, the degree of (−1) of the code elements is 2 at most, and since secondary harmonics are emphasized, the amount of phase shift is 180° at most. However, it is also possible to synthesize the composite modulation code, codeX, from three codes, code1, code2, and code3. When codeX is composed from three codes, the degree of (−1) of code elements is 3 at most, and therefore a phase shift amount of 270° is assigned to a degree of 3. In this case, such a waveform having a phase shift amount of 270° shown in FIG. 16 is stored in the waveform storage means 26 beforehand, and outputted.

As codeX as the composite modulation code, various codes can be combined as in the first embodiment. When complementary type codes such as Golay codes are used, transmission and reception are performed twice or more with an orthogonal complementary pair of codes and an operation of adding the reception signals is conducted in the signal processing means 46. The demodulators 40 and 44 can be disposed in the same manner as in the second or third embodiment. It is also possible to directly store codeY in the composite code storage means 90 as in the fourth embodiment shown in FIG. 12.

Sixth Embodiment

The ultrasonic diagnostic apparatus according to the sixth embodiment of the present invention will be explained with reference to FIGS. 17 to 19. In the fifth embodiment mentioned above, because fundamental wave components are contained in the reception signals after the demodulation, they are cut with a band control filter 140. In this embodiment, however, harmonic components are emphasized while offsetting the fundamental wave components by performing encoded transmission and reception twice and adding the reception signals.

Figure 17:
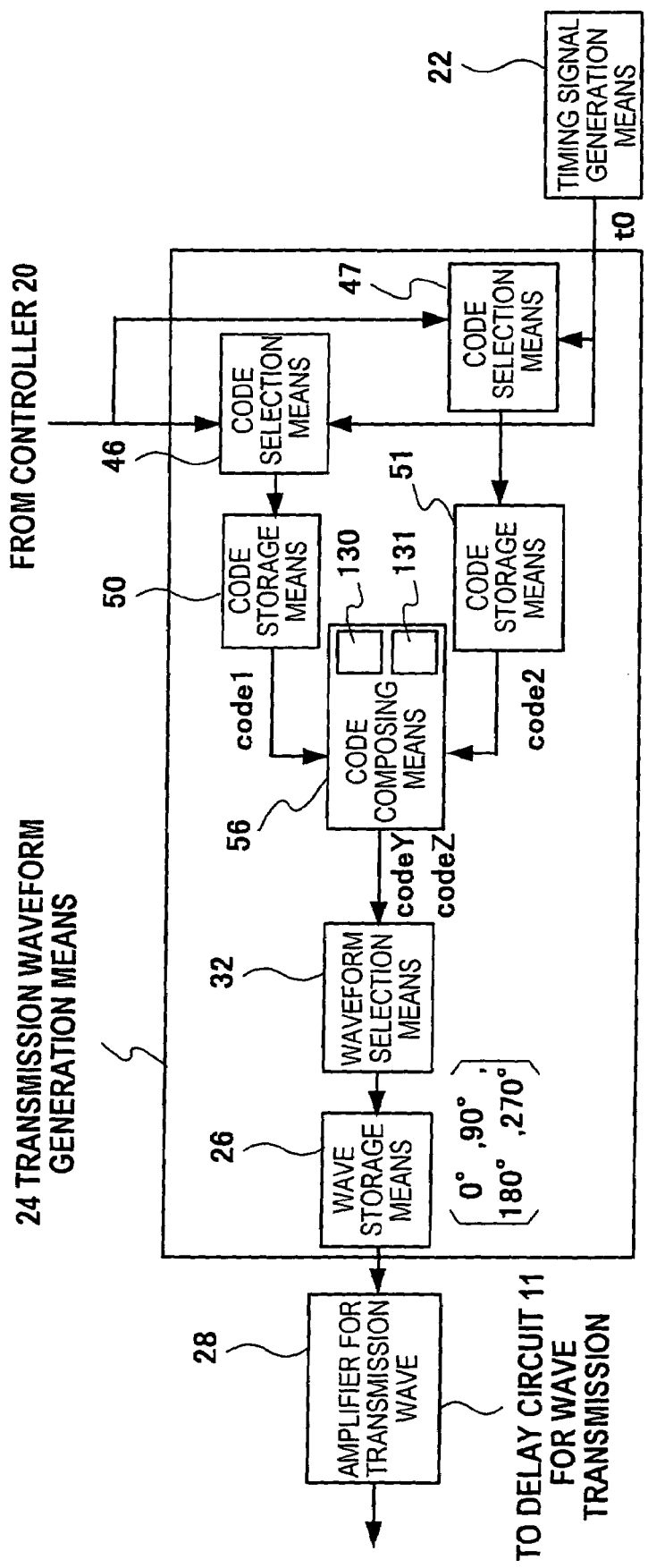
[FIG. 17]
Figure 18:
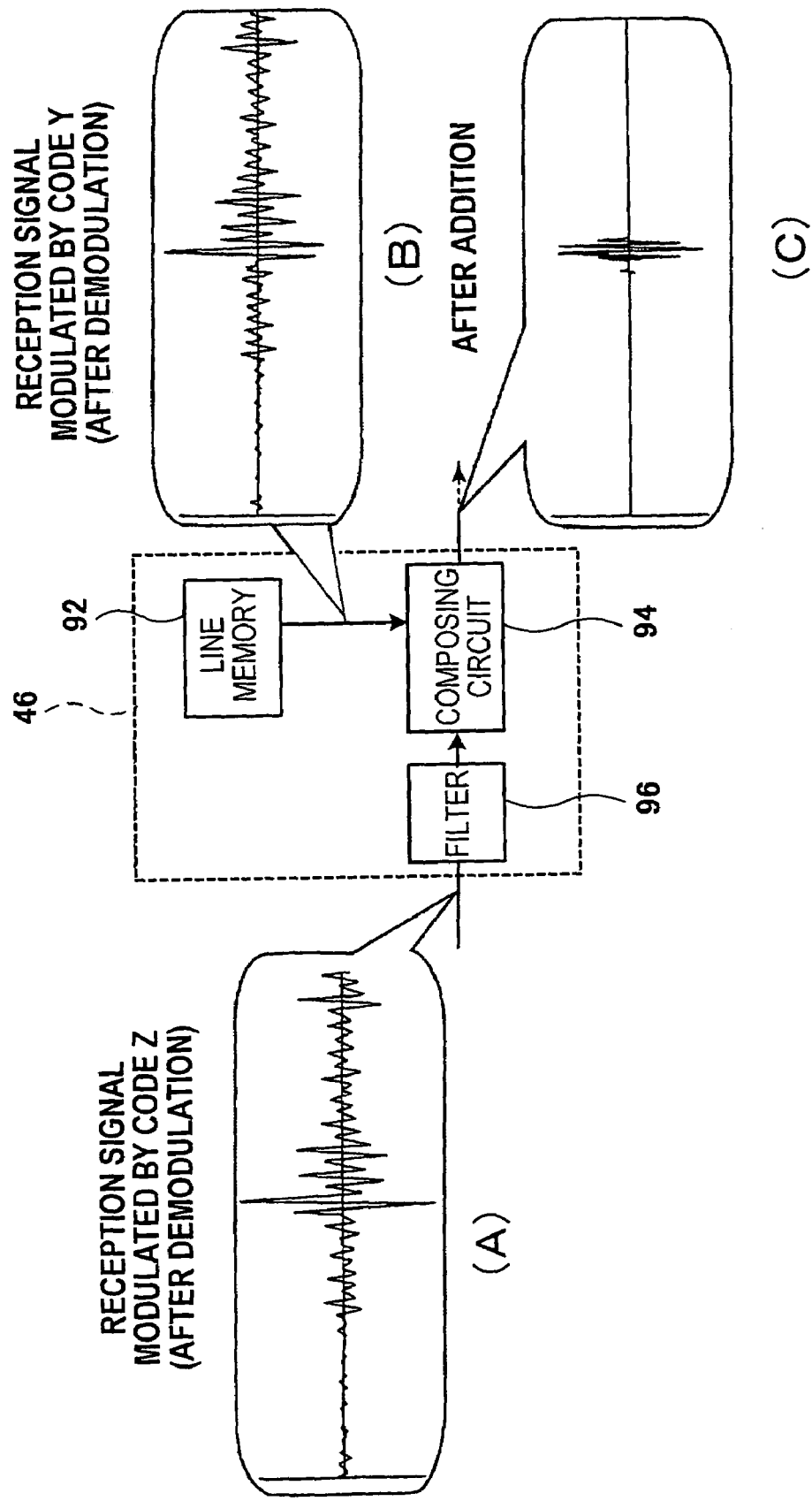
[FIG. 18]

Although the ultrasonic diagnostic apparatus of this embodiment has substantially the same configuration as that of the fifth embodiment as shown in FIG. 17, the code composing means 56 has, in addition to the phase modulation means 130 which generates the composite modulation code, codeY (first composite modulation code), the second code generation means 131 which further shifts the phase of each code element of the first composite modulation code, codeY, by a given amount to generate the second composite modulation code, codeZ. Further, as shown in FIG. 18, the signal processing means 46 has a band control filter 96, a line memory 92 which temporarily stores reflection signals outputted from the band control filter 96, and a synthesis circuit 94 which adds and composes the reflection signals outputted from the band control filter 96 and the reflection signals outputted from the line memory 92. In this embodiment, because harmonic components are emphasized with offsetting fundamental wave components by performing transmission and reception twice and adding reception signals, the band control filter 96 is basically unnecessary. However, the band control filter 96 was disposed in this example in order to remove the fundamental wave components which cannot be offset due to movement of the object.

Figure 19:
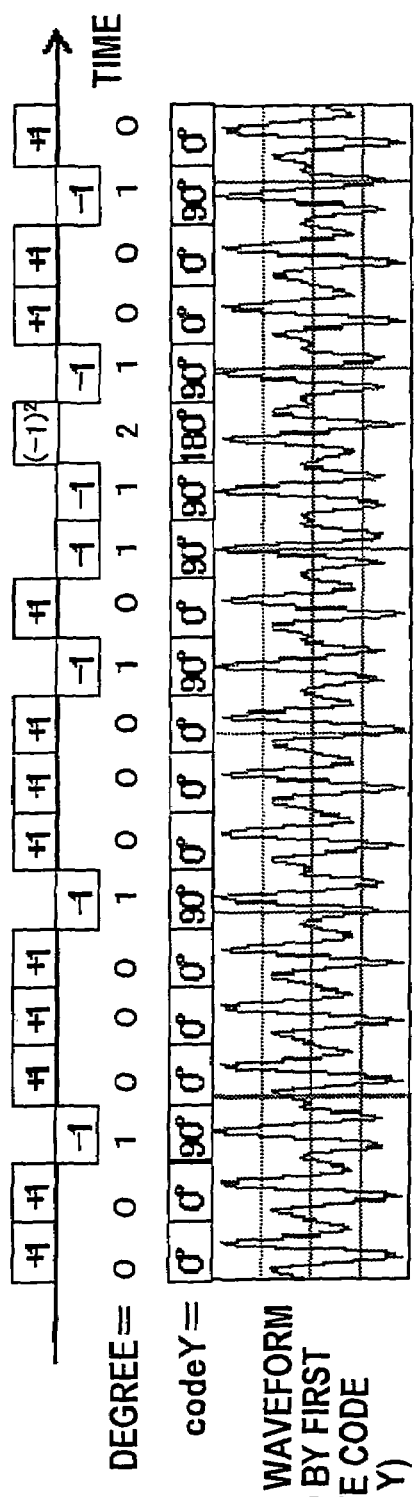
[FIG. 19]

The phase modulation means 130 of the code composing means 56 generates the composite modulation code, codeY, shown in FIG. 19 as the first composite modulation code by an operation explained for the fifth embodiment. Subsequently, the second code generation means 131 generates the second composite modulation code, codeZ, which corresponds to the first composite modulation code, codeY, in which phase of each code element is shifted by 180°. For example, the phases of code elements of the first composite modulation code, codeY, and the phases of code elements of the second composite modulation code, codeZ, are as follows.

<Phases of Code Elements of the First Composite Modulation Code, CodeY>
{0°, 0°, 90°, 0°0°, 0°, 90°, 0°, 0°, 0°, 90°, 0°, 90°, 90°, 180°, 90°, 0°, 0°, 0°, 0°}

<Phases of Code Elements of the Second Composite Modulation code, CodeZ>

{180°, 180°, 270°, 180°, 180°, 180°, 270°, 180°, 270°, 270°, 0°, 270°, 180°, 180°, 270°, 180°}

The procedure of encoded transmission and reception using such first composite modulation code, codeY, and second composite modulation code, codeZ, will be explained. First, transmission signals with the waveform of the first composite modulation code, codeY, are supplied from the transmission means 12 to the probe 10, and encoded ultrasonic beams are thereby transmitted from the probe 10. Encoded reflection echo signals reflected by microbubbles of the ultrasonic contrast agent are received by the probe 10. The encoded reflection echo signals converted into electric signals with each oscillator of the probe 10 are subjected to a two-step demodulation operation with decode1 and decode2 and a phasing addition operation performed by the reception means 12 as in the fifth embodiment, and outputted to the signal processing means 46 as the first reflection signals. In the first reflection signals, harmonics are emphasized as explained in the fifth embodiment. The first reflection signals pass through the band control filter 96 and then are temporarily retained in the line memory 92. A waveform of a reception signal retained in the line memory 92 is shown in FIG. 18(B).

Then, transmission signals with the waveform of the second composite modulation code, codeZ, are supplied to the probe 10 from the transmission means 12, and encoded ultrasonic beams are thereby transmitted from the probe 10. The scanning line of the encoded ultrasonic beams is controlled so that it should be the same as the scanning line of the encoded transmission and reception with the first composite modulation code, codeY. Then, the reflection echo signals are received by the probe 10, and the reception signals are subjected to a two-step demodulation operation with decode1 and decode2 and phasing addition similar to those used for the first composite modulation code, codeY, and then outputted to the signal processing means 46. The waveform of the reception signals is shown in FIG. 18(A). Because in this reception signal waveform, the phases of codeZ are shifted by 180° with respect to codeY, the polarity of the fundamental wave components is reversed, but the polarity of the harmonic components is not reversed compared with the reception signal waveform using codeY (FIG. 18(B)) retained in the line memory 92. Therefore, by adding the reflection signals based on the composite modulation code, codeY, and the reflection signals based on the composite modulation code, codeZ in the synthetic circuit 94, the fundamental wave components are offset, and the harmonic components are emphasized by the addition (FIG. 18(C)). An ultrasonogram of harmonic components is reconstructed according to the output of the synthetic circuit 94.

According to this embodiment, phase of each code element of the composite modulation code, codeZ, is shifted by 180° with respect to phase of each code element of codeY, thus the polarities of the fundamental wave components of the reflection signals of these are inversed, and therefore the fundamental wave components can be suppressed by adding the both. Because the polarity of the secondary harmonic components is not inversed, they are emphasized by addition. Therefore, the S/N ratio of secondary harmonic components becomes larger, and thus the image resolution of the ultrasonogram can be improved. Moreover, because the band control filter 96 is disposed, even when fundamental wave components which cannot be offset only by addition remain due to movement of the object during two times of transmission and reception, they can be eliminated by the band control filter 96. Therefore, residual fundamental wave constituting time side lobe for the harmonics desired to be emphasized can be reduced.

For this embodiment, an example of generating two composite modulation codes of which phases are shifted by 180° to each other and performing two times of encoded transmission and reception for the same scanning line was explained. However, this embodiment is not limited to this example, and it is also possible to perform three times or more of transmission and reception. In such a case, the first composite modulation code, the second composite modulation code, and a composite modulation code in which phases are shifted by 120° each as the third composite modulation code are generated by the code composing means 56. By performing three times of encoded transmission and reception with the first to third composite modulation codes for the same scanning line and adding reflection signals corresponding to those composite modulation codes, the third harmonic components can be emphasized while offsetting the fundamental wave components.

To summary, when multiple times of encoded transmission and reception are performed for the same scanning line, as the relationship of composite modulation codes for the phase, the phases can be shifted so that the fundamental wave components should be offset or reduced and harmonic components should be increased by sum of products. For example, when encoded transmission and reception are performed multiple times of A times (A is a natural number) for the same scanning line, the composite modulation code used for the B-th (B is a natural number equal to or smaller than A) encoded transmission and reception may be a composite modulation code in which phases are shifted by 360°/A with respect to those in the composite modulation code used for the (B−1)-th encoded transmission and reception. Further, by suitably choosing the number of times of encoded transmission and reception and combining phases of composite modulation codes, two or more kinds of harmonics and intermediate frequencies can be emphasized. In addition, it is also possible to suitably combine the first to fourth embodiments and modified versions thereof.

Further, although codeX is generated with a Barker code sequence etc. and codeY is generated on the basis of it in the aforementioned sixth embodiment, it is also possible to combine various codes to synthesize codeX as a composite modulation code as in the first embodiment. However, when complementary type codes such as Golay codes are used, it is necessary to repeat transmission and reception more than twice with orthogonal complementary codes to obtain one reception signal and to perform an operation of adding reception signals in the signal processing means 46. Therefore, when codeY and codeZ are used, transmission and reception are performed twice with codeY and an orthogonal complementary code, the reception signals are added to obtain reception signals corresponding to codeY, transmission and reception are further performed twice with codeZ and an orthogonal complementary code to obtain reception signals corresponding to codeZ, and the reception signals of codeY and codeZ are added in the circuit shown in FIG. 18. Therefore, when secondary harmonics are emphasized, four times of transmission and reception are needed, and when third harmonics are emphasized, six times of transmission and reception are needed.

The demodulators 40 and 44 can be disposed in the same manner as that of the second or third embodiment. Further, it is also possible to directly store codeY and codeZ in the composite code storage means 90 as in the fourth embodiment shown in FIG. 12.

The invention claimed is:

1. An ultrasonic diagnostic apparatus comprising:
a probe which transmits and receives ultrasonic waves to and from an object to be inspected;
a transmission means which outputs transmission signals for driving the probe;
a reception means which processes reception signals received by the probe; and
an image reconstruction means which reconstructs an ultrasonic image using the reception signals outputted by the reception means,
wherein:
the transmission means creates and outputs the transmission signals corresponding to a composite modulation code sequence composed from two or more modulation code sequences,
the reception means is provided with a demodulator which demodulates the modulation based on the composite modulation code sequence for the reception signals,
the demodulator comprises a first demodulator for demodulating the modulation based on the first modulation code sequence, and
a second demodulator for demodulating the modulation based on the second modulation code sequence, and the reception signals outputted by the probe are demodulated by one of the first and second demodulators, and then further demodulated by the other demodulator.

2. The ultrasonic diagnostic apparatus according to claim 1, wherein the transmission means generates the transmission signals by successively outputting waveforms on the basis of coefficients of code elements of the composite modulation code sequence.

3. The ultrasonic diagnostic apparatus according to claim 1, wherein:
the code interval of the first modulation code sequence is larger than the code interval of the second modulation code sequence, and
the first demodulator and the second demodulator have such a configuration that the reception signals outputted from the probe should be demodulated by the first demodulator and then demodulated by the second demodulator 4. The ultrasonic diagnostic apparatus according to claim 1, wherein:
the probe comprises multiple oscillators, the reception signals are outputted from each of the multiple oscillators, the reception means comprises a phasing addition means which performs phasing of the reception signals outputted from each oscillator and adds them,
the first demodulator is disposed at a position for demodulating the reception signals before phasing addition thereof performed in the phasing addition means, and
the second demodulator is disposed at a position for demodulating the reception signals after phasing addition in the phasing addition means.

5. The ultrasonic diagnostic apparatus according to claim 1, wherein:
the probe comprises multiple oscillators, the reception signals are outputted from each of the multiple oscillators, the reception means comprises a phasing addition means which performs phasing of the reception signals outputted from each oscillator and adds them, and
both the first and second demodulators are disposed at a position for demodulating the reception signals after phasing addition in the phasing addition means.

6. The ultrasonic diagnostic apparatus according to claim 1, wherein:
the probe comprises multiple oscillators, the reception signals are outputted from each of the multiple oscillators, the reception means comprises a phasing addition means which performs phasing and adding of the reception signals outputted from each oscillator, and
both the first and second demodulators are disposed at a position for demodulating the reception signal before phasing addition in the phasing addition means.

7. The ultrasonic diagnostic apparatus according to claim 1, wherein:
the code length of the second modulation code sequence is equivalent to or shorter than the code interval of the code elements constituting the first modulation code sequence, and coefficients of the code elements constituting the composite modulation code sequence are obtained by multiplying coefficient of each code element of the first modulation code sequence and each coefficient of the code elements constituting the second modulation code sequence.

8. The ultrasonic diagnostic apparatus according to claim 1, wherein the transmission means comprises a code storage means in which coefficients of multiple kinds of modulation code sequences are stored beforehand, a selection means which selects two or more modulation code sequences from those stored in the code storage means, and a composing means which composes the two or more modulation code sequences with adjusting the coefficients of them to desired code intervals to generate a composite modulation code sequence.

9. The ultrasonic diagnostic apparatus according to claim 1, wherein the transmission means comprises a composite code storage means in which multiple kinds of the composite modulation code sequences are stored beforehand, and a selection means which selects one composite modulation code sequence from those stored in the composite code storage means.

10. An ultrasonic diagnostic apparatus comprising:
a probe which transmits and receives ultrasonic waves to and from an object to be inspected;
a transmission means which outputs transmission signals for driving the probe;
a reception means which processes reception signals received by the probe to obtain reception signals of which harmonics are emphasized; and
an image reconstruction means which reconstructs an ultrasonic harmonic image using the reception signals outputted by the reception means,
wherein:
the transmission means creates and outputs the transmission signals corresponding to a composite modulation code sequence composed from two or more modulation code sequences and having phase shift amounts with respect to the fundamental wave as values of code elements,
the reception means is provided with a demodulator which demodulates the modulation based on the composite modulation code sequence for the reception signals,
the composite modulation code sequence is a composite modulation code sequence composed from a first modulation code sequence and a second modulation code sequence,
the reception means has a first demodulator for demodulating the modulation based on the first modulation code sequence for the reception signals, and a second demodulator for demodulating the modulation based on the second modulation code sequence for the reception signals, and the first and second demodulators have such a configuration that the reception signals should be demodulated by one of the first and second demodulators, and then further demodulated by the other demodulator.

11. The ultrasonic diagnostic apparatus according to claim 10, wherein the transmission means generates the transmission signals by successively outputting waveforms representing the phase shift amounts as values of the code elements of the composite modulation code sequence.

12. The ultrasonic diagnostic apparatus according to claim 10, wherein the coefficients of the code elements of the first and second modulation code sequences are two values of +1 and −1, and the phase shift amounts as the values of the code elements of the composite modulation code sequence are phase shift amounts corresponding to degrees of multiplied −1 in multiplication of the first and second modulation code elements.

13. The ultrasonic diagnostic apparatus according to claim 10, wherein phase shift amounts of the code elements of the composite modulation code sequence are determined as $(180°/M) \times N$, wherein M is a degree of harmonic to be emphasized, and N is the degree of −1.

14. The ultrasonic diagnostic apparatus according to claim 10, wherein the reception means comprises a filter for eliminating fundamental wave components from the reception signals demodulated by the first and second demodulators.

15. The ultrasonic diagnostic apparatus according to claim 10, wherein:

the transmission means outputs waveform signals of the composite modulation code sequence and waveform signals of another composite modulation code sequence in which the phase shift amounts of the code elements of the composite modulation code sequence are each further shifted by a predetermined amount of phase, and the reception means has a reception signal composing means which offsets fundamental wave components by composing reception signals of waveform signals first outputted among the transmission signals of two of the composite modulation code sequences with reception signals of waveform signals outputted afterward.

16. The ultrasonic diagnostic apparatus according to claim 10, wherein the transmission means comprises a storage means which stores the first and second modulation code sequences, a phase difference determination means which receives the first and second modulation code sequences from the storage means to count the degree of −1 and assigns a predetermined phase shift amount depending on the degree, and a waveform storage means which stores multiple kinds of waveforms corresponding to predetermined phase shift amounts and outputs a waveform corresponding to the phase shift amount determined by the phase difference determination means as transmission signals.

17. The ultrasonic diagnostic apparatus according to claim 10, wherein the transmission means comprises a composite code storage means which stores multiple kinds of composite modulation code sequences beforehand, and a selection means which selects one composite modulation code sequence from those stored in the composite code storage means.

18. The ultrasonic diagnostic apparatus according to claim 10, wherein:

the code interval of the first modulation code sequence is larger than the code interval of the second modulation code sequence, and the first and second demodulators are disposed so that the reception signals outputted from the probe should be demodulated by the first demodulator and then demodulated by the second demodulator.

* * * * *